United States Patent
Sinclair et al.

(10) Patent No.: US 10,421,733 B2
(45) Date of Patent: Sep. 24, 2019

(54) METHODS OF CHEMICAL SYNTHESIS OF DIAMINOPHENOTHIAZINIUM COMPOUNDS INCLUDING METHYLTHIONINIUM CHLORIDE (MTC)

(71) Applicant: WISTA LABORATORIES LTD., Singapore (SG)

(72) Inventors: James Peter Sinclair, Old Aberdeen (GB); Sarah Louise Nicoll, Old Aberdeen (GB); John Mervyn David Storey, Old Aberdeen (GB)

(73) Assignee: WISTA LABORATORIES LTD., Singapore (SG)

( * ) Notice: Subject to any disclaimer, the term of this patent is extended or adjusted under 35 U.S.C. 154(b) by 0 days.

(21) Appl. No.: 16/040,964

(22) Filed: Jul. 20, 2018

(65) Prior Publication Data

US 2018/0327372 A1 Nov. 15, 2018

Related U.S. Application Data

(62) Division of application No. 15/674,229, filed on Aug. 10, 2017, now Pat. No. 10,047,062, which is a division of application No. 15/027,400, filed as application No. PCT/GB2014/053007 on Oct. 6, 2014, now Pat. No. 9,765,042.

(30) Foreign Application Priority Data

Oct. 7, 2013 (GB) .................................. 1317702.7

(51) Int. Cl.
C07D 279/18 (2006.01)
C07C 381/02 (2006.01)

(52) U.S. Cl.
CPC .......... C07D 279/18 (2013.01); C07C 381/02 (2013.01)

(58) Field of Classification Search
CPC ............................ C07D 279/18; C07C 381/02
USPC ......................................................... 544/36
See application file for complete search history.

(56) References Cited

U.S. PATENT DOCUMENTS

| 204,796 A | 6/1878 | Caro |
| 6,953,794 B2 | 10/2005 | Wischik et al. |
| 2007/0191352 A1 | 8/2007 | Wischik et al. |

FOREIGN PATENT DOCUMENTS

| CN | 1970548 A | 5/2007 |
| DE | 1886 | 12/1877 |
| DE | 45839 | 12/1888 |
| DE | 46805 | 3/1889 |
| DE | 47345 | 5/1889 |
| DE | 84849 | 12/1895 |
| EP | 0 510 668 A2 | 4/1992 |
| GB | 2 373 787 A | 10/2002 |
| WO | WO-96/30766 A1 | 10/1996 |
| WO | WO-98/31219 A1 | 7/1998 |
| WO | WO-01/96322 A1 | 12/2001 |
| WO | WO-02/055720 A2 | 7/2002 |
| WO | WO-2006/032879 A2 | 3/2006 |
| WO | WO-2007/110629 A1 | 10/2007 |
| WO | WO-2010/130977 A1 | 11/2010 |

OTHER PUBLICATIONS

Bernthsen; "Studien in der Methylenblaugruppe," Justus Liebig's Annalen der Chemie, Band 230, pp. 137-211 (Jul. 1885) (with English abstract).

Bernthsen; "Studien in der Methylenblaugruppe," Justus Liebig's Annalen der Chemie, Band 230:73-136 (Aug. 1885) (with English abstract).

Bernthsen; "Studien in der Methylenblaugruppe," Justus Liebig's Annalen der Chemie, Band 251, pp. 1-96 (Nov. 1888) (with English abstract).

Bonneau et al; "Purification des colorants thiaziniques, Azur A, Azur B, Azur C, par une méthode de partage"; Talanta, 14:121-122 (1967) (with English translation).

Braswell; "Evidence for Trimerization in Aqueous Solutions of Methylene Blue"; The Journal of Physical Chemistry, 72(7): 2477-2483 (Jul. 1968).

Colour Index, vol. 4 (3rd Edition, 1971), p. 4470, Entry No. 52015.

Fierz-David et al., "Grundlegende Operationen der Farbenchemie," 1943, pp. 294-298.

Fierz-David, et al.; "F. oxazine and thiazine dyes"; Fundamental Processes of Dye Chemistry, 308-314 (1949); Interscience, London.

Fierz-David, et al.; "Methylene blue from dimethylaniline" The Fundamental Processes of Dye Chemistry by Fierz-David, [Translated by Mason, F.A.]. pp. 174-178 (1921); D. Van Nostrand Company, New York.

(Continued)

*Primary Examiner* — Kahsay Habte
(74) *Attorney, Agent, or Firm* — Foley & Lardner LLP

(57) ABSTRACT

Methods of synthesizing and purifying certain 3,7-diaminophenothiazin-5-ium compounds (referred to herein as "diaminophenothiazinium compounds") including Methylthioninium Chloride (MTC) (also known as Methylene Blue) are provided.

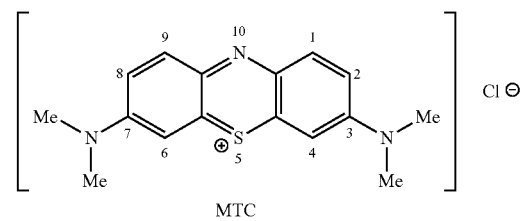

MTC

26 Claims, 4 Drawing Sheets

(56) References Cited

OTHER PUBLICATIONS

Guttmann et al.; "Über die Wirkung des Methylenblau bei Malaria" Berliner Klinische Wochenschrift, 39:953-956 (Sep. 28, 1891).

Kubáň et al.; "Preparation of highly pure methylene blue compositions by an extraction procedure"; Chemicke Listy 79:1200-1205 (1985) (with English abstract).

Leventis, et al.; "Synthesis of Substituted Phenothiazines Analogous to Methylene Blue by Electrophilic and Nucleophilic Aromatic Substitutions in Tandem. A Mechanistic Perspective."; Tetrahedron, 53(29): 10083-10092 (1997).

Lillie, et al.; "Zinc Chloride Methylene Blue. I. Biological Stain History, Physical Characteristics and Approximation of Azure B Content of Commercial Samples"; Stain Technology, 54(1): 33-39 (1979).

Löhr et al.; "The Azure Dyes: Their Purification and Physicochemical Properties. II. Purification of Azure B."; Stain Technology, 50(3): 149-156 (1975).

Marshall et al.; "Metal Contaminants in Commercial Thiazine Dyes"; Stain Technology, 50(3): 143-147 (1975).

Marshall, et al.; "The Purification of Methylene Blue and Azure B by Solvent Extraction and Crystallization"; Stain Technology, 50(6): 375-381 (1976).

Michaelis et al.; "Semiquinone Radicals of the Thiazines"; J. Am. Chem. Soc., 62: 204-211 (Jan. 1940).

PCT International Search Report issued in application PCT/GB2014/053007 dated Mar. 19, 2015; 5 pages.

Rengelshausen et al.; "Pharmacokinetic interaction of chloroquine and methylene blue combination against malaria"; Eur J Clin Pharmacol, 60:709-715 (Oct. 2004).

Russell, R., "One-Pot Synthesis Aids Scale-Up and Data Collection", Pharmaceutical Technology, Advanstar Communications, Inc, Nov. 2003, pp. 17 and 22.

Schirmer et al.; "Methylene blue as an antimalarial agent"; Redox Report, 8(5):272-275 (2003).

Scheme 1 – Synthesis by a 3-pot process

Scheme 2a: Two reactor MTC process

Scheme 2b: Two reactor MTC process

METHODS OF CHEMICAL SYNTHESIS OF DIAMINOPHENOTHIAZINIUM COMPOUNDS INCLUDING METHYLTHIONINIUM CHLORIDE (MTC)

CROSS-REFERENCE TO RELATED APPLICATIONS

This application is a divisional of U.S. application Ser. No. 15/674,229, filed on Aug. 10, 2017, which is a divisional of U.S. application Ser. No. 15/027,400 filed on Apr. 5, 2016, now U.S. Pat. No. 9,765,042, issued on Sep. 19, 2017, which is the U.S. National Phase of International Application PCT/GB2014/053007, filed Oct. 6, 2014, which was published in English as WO 2015/052496 on Apr. 16, 2015; and claims priority to U.K. Application GB 1317702.7, filed Oct. 7, 2013. The foregoing are entirely incorporated by reference.

TECHNICAL FIELD

This invention pertains generally to the field of chemical synthesis and purification, and more specifically to methods of synthesizing and purifying certain 3,7-diamino-phenothiazin-5-ium compounds (referred to herein as "diaminophenothiazinium compounds") including Methylthioninium Chloride (MTC) (also known as Methylene Blue). The present invention also pertains to the resulting (high purity) compounds, compositions comprising them (e.g., tablets, capsules), and their use in methods of inactivating pathogens, and methods of medical treatment and diagnosis, etc., for example, for tauopathies, Alzheimer's disease (AD), skin cancer, melanoma, viral diseases, bacterial diseases and protozoal diseases.

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Methylthioninium Chloride (MTC) (Also Known as Methylene Blue)

Methylthioninium Chloride (MTC) (also known as Methylene Blue (MB); methylthionine chloride; tetramethylthionine chloride; 3,7-bis(dimethylamino) phenothiazin-5-ium chloride; C.I. Basic Blue 9; tetramethylthionine chloride; 3,7-bis(dimethylamino) phenazathionium chloride; Swiss blue; C.I. 52015; C.I. Solvent Blue 8; aniline violet; and Urolene Blue®) is a low molecular weight (319.86), water soluble, tricyclic organic compound of the following formula:

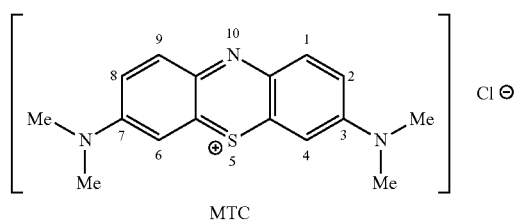

MTC

Methylthioninium Chloride (MTC) (also known as Methylene Blue), perhaps the most well-known phenothiazine dye and redox indicator, has also been used as an optical probe of biophysical systems, as an intercalator in nanoporous materials, as a redox mediator, and in photoelectrochomic imaging.

See, for example, Colour Index (Vol. 4, 3rd edition, 1971) and Lillie et al., 1979, and references cited therein.

MTC is currently used to treat methemoglobinemia (a condition that occurs when the blood cannot deliver oxygen where it is needed in the body). MTC is also used as a medical dye (for example, to stain certain parts of the body before or during surgery); a diagnostic (for example, as an indicator dye to detect certain compounds present in urine); a mild urinary antiseptic; a stimulant to mucous surfaces; a treatment and preventative for kidney stones; and in the diagnosis and treatment of melanoma.

MTC has been used to treat malaria either singly (Guttmann & Ehrlich, 1891) or in combination with chloroquine (Schirmer et al. 2003; Rengelhausen et al. 2004). Malaria in humans is caused by one of four protozoan species of the genus *Plasmodium*: *P. falciparum, P. vivax, P. ovale*, or *P. malariae*. All species are transmitted by the bite of an infected female Anopheles mosquito. Occasionally, transmission occurs by blood transfusion, organ transplantation, needle-sharing, or congenitally from mother to fetus. Malaria causes 300-500 million infections worldwide and approximately 1 million deaths annually. Drug resistance, however is a major concern and is greatest for *P. falciparum*, the species that accounts for almost all malaria-related deaths. Drugs or drug combinations that are currently recommended for prophylaxis of malaria include chloroquine/ proguanil hydrochloride, mefloquine, doxycycline and primaquine.

MTC (under the name Virostat, from Bioenvision Inc., New York) has shown potent viricidal activity in vitro. Specifically Virostat is effective against viruses such as HIV and West Nile Virus in laboratory tests. West Nile virus (WNV) is a potentially serious illness affecting the central nervous system. The large majority of infected people will show no visible symptoms or mild flu-like symptoms such as fever and headache. About one in 150 will develop severe symptoms including tremors, convulsions, muscle weakness, vision loss, numbness, paralysis or coma. Generally, WNV is spread by the bite of an infected mosquito, but can also spread through blood transfusions, organ transplants, breastfeeding or during pregnancy from mother to child. Virostat is also currently in clinical trials for the treatment of chronic Hepatitis C. Hepatitis C is a viral infection of the liver. The virus, HCV, is a major cause of acute hepatitis and chronic liver disease, including cirrhosis and liver cancer. HCV is spread primarily by direct contact with human blood. The major causes of HCV infection worldwide are use of unscreened blood transfusions, and re-use of needles and syringes that have not been adequately sterilized. The World Health Organization has declared hepatitis C a global health problem, with approximately 3% of the world's population infected with HCV and it varies considerably by region. The prevalence in the US is estimated at 1.3% or approximately 3.5 million people. Egypt contains the highest prevalence of hepatitis C in the world, estimated at over 20% of the nation's approximately 62 million people.

MTC, when combined with light, can prevent the replication of nucleic acid (DNA or RNA). Plasma, platelets and red blood cells do not contain nuclear DNA or RNA. When MTC is introduced into the blood components, it crosses bacterial cell walls or viral membrane then moves into the interior of the nucleic acid structure. When activated with light, the compounds then bind to the nucleic acid of the viral or bacterial pathogen, preventing replication of the DNA or RNA. Because MTC is designed to inactivate pathogens, it has the potential to reduce the risk of transmission of pathogens that would remain undetected by testing.

MTC and derivatives thereof (e.g., "diaminophenothiazinium compounds") have been found to be useful in the treatment of tauopathies (such as, for example, Alzheimer's disease) (see, for example, Wischik, C. M., et al., 1996, 2002).

MTC was first described in a German Patent in 1877 (Badische Anilin- und Soda-Fabrik, 1877). In that patent, MTC was synthesized by nitrosylation of dimethylaniline, subsequent reduction to form N,N-dimethyl-1,4-diaminobenzene, and subsequent oxidative coupling in the presence of hydrogen sulphide ($H_2S$) and iron(III) chloride ($FeCl_3$).

Bernthsen described subsequent studies of MTC and methods for its synthesis (see Bernthsen, 1885a, 1885b, 1889).

Fierz-David and Blangley, 1949, also describes methods for the synthesis of MTC from dimethylaniline, as illustrated in the following scheme

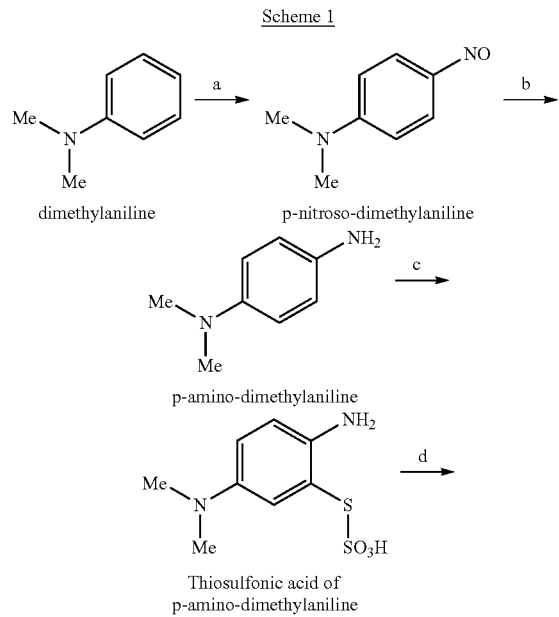

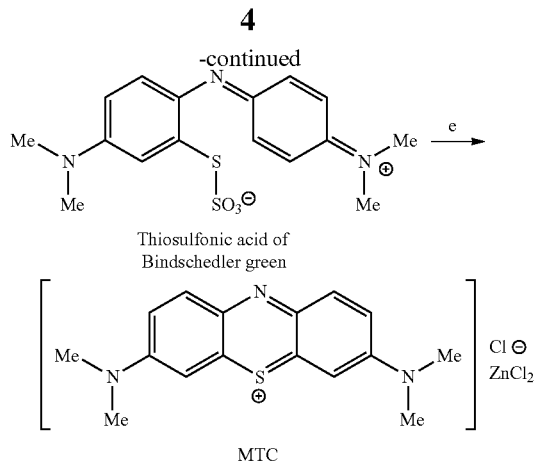

In step (a), nitrosodimethylaniline is prepared from dimethylaniline by treatment with nitrite ($NaNO_2$) in aqueous acid (HCl) solution. In step (b), the nitroso compound is reduced to form p-aminodimethylaniline using additional aqueous acid (HCl) solution using zinc dust. The metal residue after step (b) is removed by filtration and the filtrate is oxidised in the presence of thiosulfonic acid, sulphuric acid and non-reducing zinc chloride solution, step (c). Further oxidation in the presence of dimethylaniline results in the thiosulfonic acid of Bindschedlers green, step (d). The ring is then closed using manganese dioxide or copper sulphate to form methylene blue. More specifically, a clear neutral solution of p-aminodimethylaniline is acidified ($H_2SO_4$), and a non reducing zinc chloride solution is added ($ZnCl_2$ with $Na_2Cr_2O_7$). Aqueous aluminium sulphate ($Al_2(SO_4)$) and crystalline sodium thiosulphate ($Na_2S_2O_3$) are added. Aqueous sodium dichromate ($Na_2Cr_2O_7$) is added. The mixture is heated by dry steam. Aqueous acidic (HCl) dimethylaniline is then added. Aqueous sodium dichromate ($Na_2Cr_2O_7$) is added. The mixture is heated with dry steam, and becomes dark greenish-blue in colour due to the formation of the thiosulfonic acid of Bindschedler green. An aqueous slurry of manganese dioxide or copper sulfate is added, and the mixture heated by dry steam, and the dye precipitates from the concentrated zinc chloride solution. To recover the dye from the mixture it is cooled and acidified ($H_2SO_4$) to dissolve the aluminium, manganese and chromium salts. The mixture is cooled further and the crude dye collected by filtration. Purification from water, sodium chloride and zinc chloride gives the zinc double salt of methylene blue as bronzy red crystals.

Very similar synthesis methods are described in the Colour Index (Vol. 4, 3rd edition, 1971), p. 4470.

Masuya et al., 1992, describe certain phenothiazine derivatives, and methods for their preparation and use in photodynamic therapy of cancer and in immunoassays utilizing chemiluminescence. The compounds are prepared by routes similar to those discussed above.

Leventis et al., 1997, describe methods for the synthesis of certain MTC analogs, which employ phenothiazine as a starting material and which add the desired 3,7-substituents by halogenation followed by amination. The authors assert that MTC is synthesized commercially by oxidation of N,N-dimethyl-p-phenylene diamine with $Na_2Cr_2O_7$ in the presence of $Na_2S_2O_3$, followed by further oxidation in the presence of N,N-dimethylamine.

Fierz-David et al., 1949, describes the synthesis of the zinc chloride double salt of MTC and the removal of zinc by chelation with sodium carbonate followed by filtration to generate zinc free methylene blue. However, the authors acknowledge that this technique cannot be used on a large scale, because the yields are poor.

Methods for synthesizing high purity MTC and its derivatives have been proposed in WO 2006/032879. The compounds are synthesized according to the scheme shown in FIG. 1.

These steps can be summarised as follows: (i) nitrosylation (NOS), (ii) nitrosyl reduction (NR), (iii) thiosulfonic acid formation (TSAF), (iv) oxidative coupling (OC), (v) ring closure (RC), and recrystallization (RX). A variant is also described, in which the thiosulfonic acid of Bindshedler's Green intermediate (compound 5) is not isolated by filtration.

The inventors have now developed alternative and improved methods for the synthesis of diaminophenothiazinium compounds (including, in particular, MTC). The new methods result in higher yields, have shorter reaction times and a higher throughput, require less energy input and generate less waste. The compounds obtained have high purity levels.

SUMMARY OF THE INVENTION

One aspect of the present invention pertains to methods of synthesis of diaminophenothiazinium compounds.

Another aspect of the invention pertains to diaminophenothiazinium compounds which are obtained by, or obtainable by, a method as described herein, and to compositions comprising those compounds. Another aspect relates to these compounds and/or compositions for use in a method of treatment of the human or animal body by therapy, for example in respect of any of the diseases or indications discussed herein.

As will be appreciated by one of skill in the art, features and preferred embodiments of one aspect of the invention will also pertain to other aspects of the invention.

DETAILED DESCRIPTION

Compounds

Figure 1:
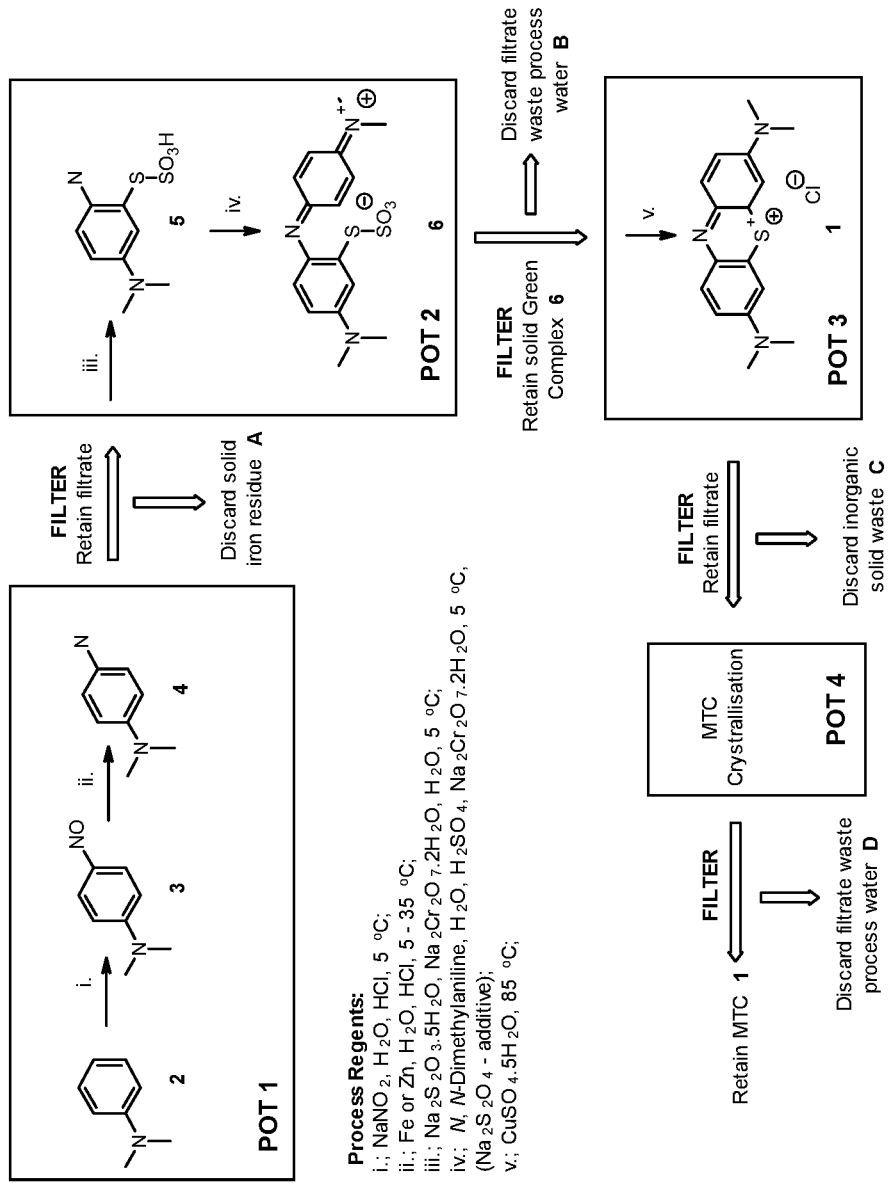
FIG. 1 shows a scheme for synthesizing high purity MTC and its derivatives as proposed in WO 2006/032879.

In general, the present invention pertains to methods for the preparation of certain 3,7-diamino-phenothiazin-5-ium compounds of the following formula, collectively referred to herein as "diaminophenothiazinium compounds":

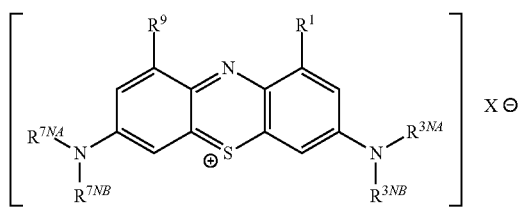

wherein:
each of $R^1$ and $R^9$ is independently selected from: —H; $C_{1-4}$alkyl; $C_{2-4}$alkenyl; and halogenated $C_{1-4}$alkyl;
each of $R^{3NA}$ and $R^{3NB}$ is independently selected from: $C_{1-4}$alkyl; $C_{2-4}$alkenyl; and halogenated $C_{1-4}$alkyl;
each of $R^{7NA}$ and $R^{7NB}$ is independently selected from: $C_{1-4}$alkyl; $C_{2-4}$alkenyl; and halogenated $C_{1-4}$alkyl; and
X is one or more anionic counter ions to achieve electrical neutrality.

The above structure is only one of many equivalent resonance structures, some of which are shown below, and all of which are intended to be encompassed by the above structure:

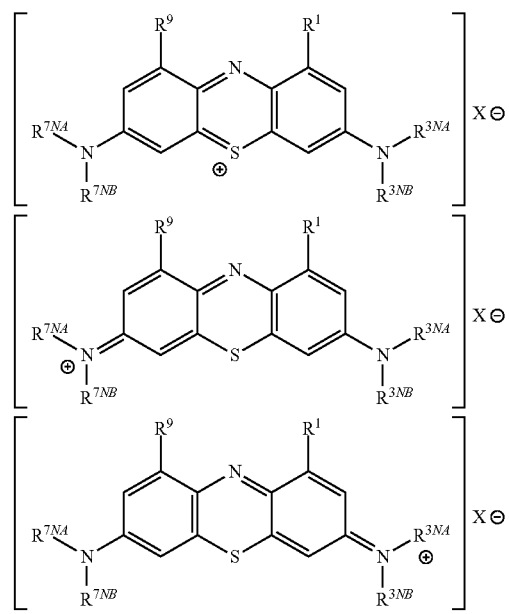

In some embodiments, the $C_{1-4}$alkyl groups are selected from: linear $C_{1-4}$alkyl groups, such as -Me, -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In some embodiments, the $C_{2-4}$alkenyl groups are selected from linear $C_{1-4}$alkenyl groups, such as —CH=CH$_2$ (vinyl) and —CH$_2$CH=CH$_2$ (allyl).

In some embodiments, the halogenated $C_{1-4}$alkyl groups are selected from: —CF$_3$, —CH$_2$CF$_3$, and —CF$_2$CF$_3$.

In some embodiments, each of $R^1$ and $R^9$ is independently —H, -Me, -Et, or —CF$_3$.

In some embodiments, each of $R^1$ and $R^9$ is independently —H, -Me, or -Et.

In some embodiments, each of $R^1$ and $R^9$ is independently —H.

In some embodiments, each of $R^1$ and $R^9$ is independently -Me.

In some embodiments, each of $R^1$ and $R^9$ is independently -Et.

In some embodiments, $R^1$ and $R^9$ are the same.

In some embodiments, $R^1$ and $R^9$ are different.

In some embodiments, each of $R^{3NA}$ and $R^{3NB}$ independently -Me, -Et, -nPr, -nBu, —CH$_2$CH=CH$_2$, or —CF$_3$.

In some embodiments, each of $R^{3NA}$ and $R^{3NB}$ is independently -Me or -Et.

In some embodiments, each of $R^{3NA}$ and $R^{3NB}$ is independently -Me.

In some embodiments, each of $R^{3NA}$ and $R^{3NB}$ is independently -Et.

In some embodiments, $R^{3NA}$ and $R^{3NB}$ are the same.

In some embodiments, $R^{3NA}$ and $R^{3NB}$ are different.

In some embodiments, each of $R^{7NA}$ and $R^{7NB}$ independently -Me, -Et, -nPr, -nBu, —CH$_2$CH=CH$_2$, or —CF$_3$.

In some embodiments, each of $R^{7NA}$ and $R^{7NB}$ is independently -Me or -Et.

In some embodiments, each of $R^{7NA}$ and $R^{7NB}$ is independently -Me.

In some embodiments, each of $R^{7NA}$ and $R^{7NB}$ is independently -Et.

In some embodiments, $R^{7NA}$ and $R^{7NB}$ are the same.

In some embodiments, $R^{7NA}$ and $R^{7NB}$ are different.

In some embodiments, $R^{3NA}$ and $R^{3NB}$ and $R^{7NA}$ and $R^{7NB}$ are the same.

In some embodiments, the groups —N($R^{3NA}$)($R^{3NB}$) and —N($R^{7NA}$)($R^{7NB}$) are the same.

In some embodiments, the groups —N($R^{3NA}$)($R^{3NB}$) and —N($R^{7NA}$)($R^{7NB}$) are the same, and are selected from: —NMe$_2$, —NEt$_2$, —N(nPr)$_2$, —N(Bu)$_2$, —NMeEt, —NMe(nPr), and —N(CH$_2$CH=CH$_2$)$_2$.

In some embodiments, the groups —N($R^{3NA}$)($R^{3NB}$) and —N($R^{7NA}$)($R^{7NB}$) are the same, and are selected from: —NMe$_2$ and -NEt$_2$.

In some embodiments, the groups —N($R^{3NA}$)($R^{3NB}$) and —N($R^{7NA}$)($R^{7NB}$) are other than —NMe$_2$.

In some embodiments, one or more of the carbon atoms is $^{11}$C or $^{13}$C.

In some embodiments, one or more of the carbon atoms is $^{11}$C.

In some embodiments, one or more of the carbon atoms is $^{13}$C.

In some embodiments, one or more of the nitrogen atoms is $^{15}$N.

In some embodiments, one or more or all of the carbon atoms of one or more or all of the groups $R^{3NA}$, $R^{3NB}$, $R^{7NA}$ and $R^{7NB}$ is $^{13}$C.

In some embodiments, each of the groups —N($R^{3NA}$)($R^{3NB}$) and —N($R^{7NA}$)($R^{7NB}$) is —N($^{13}$CH$_3$)$_2$.

In some embodiments, each of $R^1$ and $R^9$ is —H, and each of the groups —N($R^{3NA}$)($R^{3NB}$) and —N($R^{7NA}$)($R^{7NB}$) is —N($^{13}$CH$_3$)$_2$.

In some embodiments, each of $R^1$ and $R^9$ is —H; each of the groups —N($R^{3NA}$)($R^{3NB}$) and —N($R^{7NA}$)($R^{7NB}$) is —N($^{13}$CH$_3$)$_2$; and $X^-$ is Cl$^-$.

In some embodiments, $X^-$ is independently a halogen anion (i.e., halide).

In some embodiments, $X^-$ is independently Cl$^-$, Br$^-$, or I$^-$.

In some embodiments, $X^-$ is independently Cl$^-$.

In some embodiments, the compound is in the form of a mixed salt, for example, a ZnCl$_2$ mixed salt.

In some embodiments, $X^-$ is as defined above except that the compound is not a ZnCl$_2$ mixed salt.

Examples of such compounds include the following:

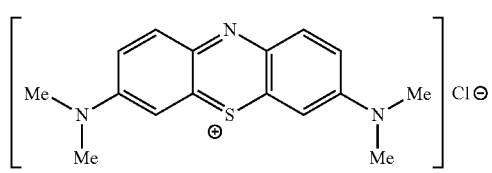

MTC
(Methylene Blue)

-continued

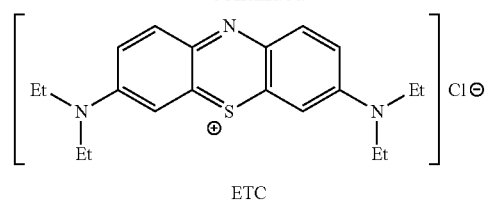

ETC

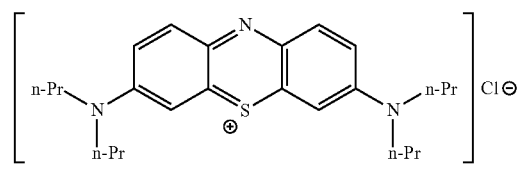

PTC

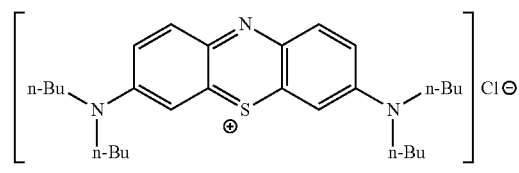

BTC

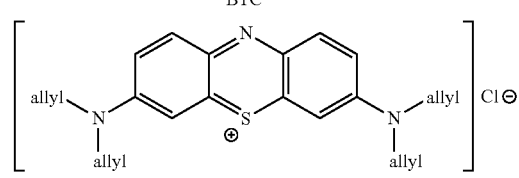

ATC

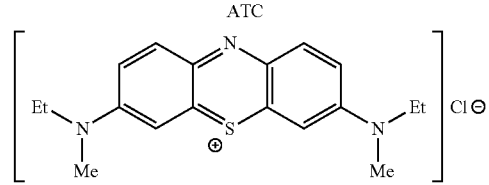

EMTC

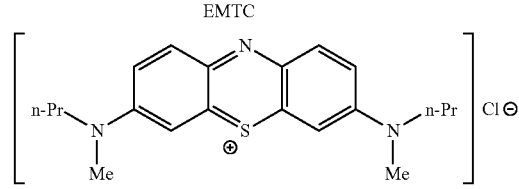

PMTC

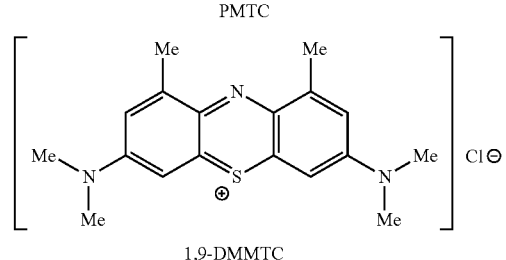

1,9-DMMTC

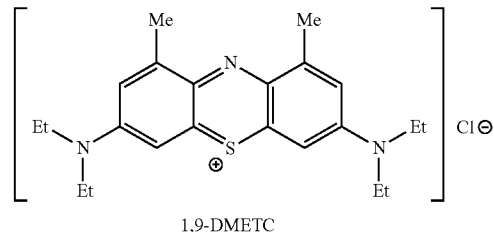

1,9-DMETC

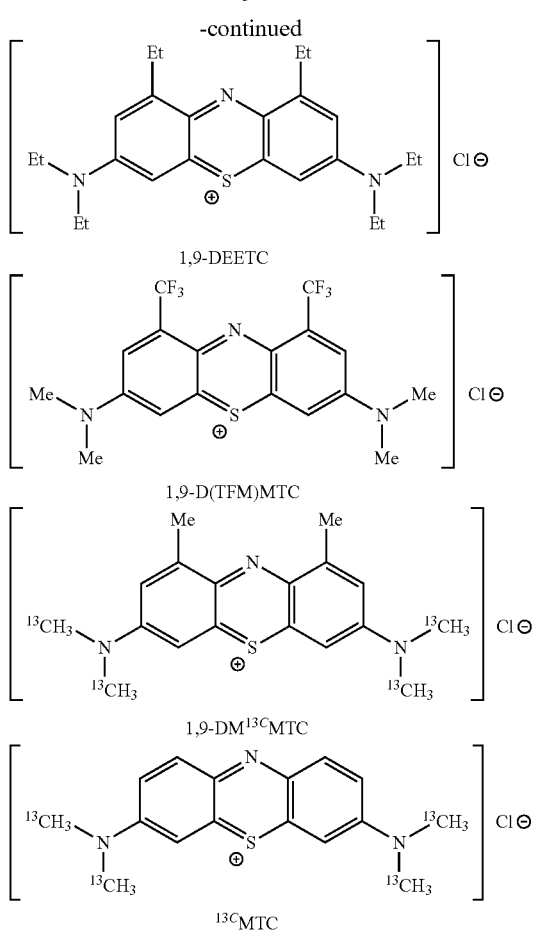

1,9-DEETC 1,9-D(TFM)MTC 1,9-DM¹³CMTC

¹³CMTC

Purity

The methods described herein may yield high purity diaminophenothiazinium compounds.

For example, many of the methods described herein yield very high purity MTC with extremely low levels of both organic impurities (e.g., of Azure B and Methylene Violet Bernthsen (MVB)) and metal impurities (e.g., meeting or exceeding the European Pharmacopoeia limits).

Thus, one aspect of the present invention pertains to a diaminophenothiazinium compound as described herein, obtained by, or obtainable by, a method as described herein. In some embodiments, the present invention pertains to MTC obtained by, or obtainable by, a method as described herein.

In some embodiments, the compound (e.g., MTC) has a purity of greater than 98%.

In some embodiments, the compound (e.g., MTC) has a purity of greater than 97%.

In some embodiments, the compound (e.g., MTC) has a purity of greater than 96%.

In some embodiments, the compound (e.g., MTC) has a purity of greater than 95%.

In some embodiments, the compound (e.g., MTC) has a purity of greater than 94%.

In some embodiments, the compound (e.g., MTC) has a purity of greater than 93%.

In some embodiments, the compound (e.g., MTC) has a purity of greater than 92%.

In some embodiments, the compound has less than 6% Azure B as impurity.

In some embodiments, the compound has less than 5% Azure B as impurity.

In some embodiments, the compound has less than 4% Azure B as impurity.

In some embodiments, the compound has less than 3% Azure B as impurity.

In some embodiments, the compound has less than 2% Azure B as impurity.

In some embodiments, the compound has less than 1% Azure B as impurity.

In some embodiments, the compound has less than 0.15% MVB as impurity.

In some embodiments, the compound has less than 0.14% MVB as impurity.

In some embodiments, the compound has less than 0.13% MVB as impurity.

In some embodiments, the compound has less than 0.10% MVB as impurity.

In some embodiments, the compound has less than 0.05% MVB as impurity.

(All percentage purities recited herein are by weight unless otherwise specified.)

In some embodiments, the compound (e.g., MTC) has an elementals purity (e.g., for Al, Cr, Zn, Cu, Fe, Mn, Ni, Mo, Cd, Sn, and Pb) that is better than the European Pharmacopoeia (EP) limits.

The term "elementals purity" referred to herein pertains to the amounts of the eleven (11) metals specified by the European Pharmacopoeia: Al, Cr, Zn, Cu, Fe, Mn, Ni, Mo, Cd, Sn, and Pb.

The European Pharmacopoeia limits referred to herein are set out in the table below:

TABLE 1

| European Pharmacopoeia Limits (μg/g) | Version EP4 (2002) | Versions EP5.4-EP7.8 (2005-2013) |
|---|---|---|
| Aluminium (Al) | 100 | 100 |
| Chromium (Cr) | 10 | 100 |
| Zinc (Zn) | 10 | 100 |
| Copper (Cu) | 100 | 300 |
| Iron (Fe) | 100 | 200 |
| Manganese (Mn) | 10 | 10 |
| Nickel (Ni) | 10 | 10 |
| Molybdenum (Mo) | 10 | 10 |
| Cadmium (Cd) | 1 | 1 |
| Tin (Sn) | 10 | 10 |
| Lead (Pb) | 10 | 10 |
| Mercury (Hg) | 1 | 1 |

In some embodiments, the compound (e.g., MTC) has an elementals purity that is better than 0.9 times the European Pharmacopoeia (EP) limits.

In some embodiments, the compound (e.g., MTC) has an elementals purity that is better than 0.5 times the European Pharmacopoeia (EP) limits.

In some embodiments, the compound (e.g., MTC) has an elementals purity that is better than 0.2 times the European Pharmacopoeia (EP) limits.

In some embodiments, the compound (e.g., MTC) has an elementals purity that is better than 0.1 times the European Pharmacopoeia (EP) limits.

(For example, 0.5 times the most recent European Pharmacopoeia (EP) limits is 50 μg/g Al, 50 μg/g Cr, 50 μg/g Zn, etc.)

All plausible and compatible combinations of the above purity grades are disclosed herein as if each individual combination was specifically and explicitly recited.

Methods of Synthesis

The present inventors have identified various improved methods of synthesising MTC and other diaminophenothiazinium compounds. In particular, they have identified improvements to the methods of WO2006/032879.

Yield

The synthesis methods described herein give high diaminophenothiazinium compound yields.

In some embodiments, the yield is greater than 35%.
In some embodiments, the yield is greater than 37.5%.
In some embodiments, the yield is greater than 40%.
In some embodiments, the yield is greater than 42.5%.
In some embodiments, the yield is greater than 45%.
In some embodiments, the yield is greater than 47.5%.

Preferably the yield reported is purely that of the diaminophenothiazinium compound and therefore takes into account the impurity profile and moisture content of the sample. In some embodiments the yields are calculated based on anhydrous weight.

In one aspect of the present invention, efficient methods of synthesis of diaminophenothiazinium compounds are provided.

One important feature of these methods is that several steps may be completed in the same reaction vessel.

For example, the nitrosyl reduction (NR) step (ii), the thiosulfonic acid formation (TSAF) step (iii) and the oxidative coupling (OC) step (iv) may all be performed in the same reaction vessel. No filtration is performed between steps (ii) and (iii).

Generally, when subsequent steps in a synthesis are said to occur in the "same reaction vessel" or the "same pot", this means that the reaction steps occur in the same container. Reagents for subsequent steps in the synthesis are simply added to the product of the previous step, without transfer of the product into another container. In particular, it excludes transfer of a reaction product to another container through a filter. For a reaction occurring entirely in the same reaction vessel, the reaction may be termed a 1-pot method. Similarly, where there is a single transfer from a first vessel to a second, this may be termed a 2-pot method. A synthesis in which there are two transfers may be termed a 3-pot method, etc.

Omission of the filtration between steps (ii) and (iii) saves time and thereby increases the reaction throughput. It also means that fewer reaction vessels are required as compared to the prior art method. Less waste water is generated, as there is no washing of the filtered solid. Elimination of this filtration step has additionally been observed to lead to an increased yield of MTC product, relative to reactions where such a filtration is performed. In preferred cases, the purity of the product compound is not compromised.

Cr(VI) is used (at least) in the oxidative coupling (OC) step. It is highly toxic, and Cr(VI) contamination is unacceptable in products destined for use in pharmacy. Further, it may destabilize the zwitterionic intermediate and impede the subsequent ring closure (RC) step, thereby reducing the yield of the final diaminophenothiazinium compound. In the WO2006/032879 method, it is therefore necessary to reduce the residual Cr(VI) to Cr(III) by addition of sodium hydrosulfite ($Na_2S_2O_4$) or by pH adjustment.

In the present method, omission of the filtration step between the NR and TSAF steps, means that the reducing agent used in the nitrosyl reduction (NR) is not removed. The present inventors have surprisingly found that this reducing agent can be used to reduce the Cr(VI) after oxidative coupling (OC).

Accordingly, in some cases, the chromate reduction step after oxidative coupling may take place in the same reaction vessel as the NR, TSAF and OC steps. In these cases there is no need to add a further reducing agent (such as $Na_2S_2O_4$) or to adjust the pH. Thus, fewer materials are used, and less waste is generated. In preferred cases, the purity of the product compound is not compromised.

In some cases, the nitrosylation step (NO) and/or ring closure (RC) may also be completed in the same reaction vessel as the nitrosyl reduction (NR), thiosulfonic acid formation (TSAF) and oxidative coupling (OC) steps.

Completing the ring closure (RC) step in the same reaction vessel is particularly advantageous, as it eliminates another filtration step from the WO2006/032879 method, thereby reducing waste, increasing yield and saving time. Further, elimination of this filtration step means that there is no need to add aqueous hydrochloric acid to the green solid filtered product to form a slurry (as in step (v) of WO2006/032879, as shown above). This further reduces material usage and waste.

Thus, in some embodiments the method of synthesis comprises the steps of, in order
  nitrosyl reduction (NR);
  thiosulfonic acid formation (TSAF);
  oxidative coupling (OC);
wherein these steps are completed in the same reaction vessel.

In some embodiments, optionally, the Zwitterionic intermediate formed in the oxidative coupling step (OC) is isolated and purified, for example by filtration, before being subjected to the ring closure step (RC).

In some embodiments, the method of synthesis comprises the steps of, in order
  nitrosylation (NOS);
  nitrosyl reduction (NR);
  thiosulfonic acid formation (TSAF);
  oxidative coupling (OC);
wherein these steps are completed in the same reaction vessel.

In some embodiments, the method of synthesis comprises the steps of, in order
  nitrosyl reduction (NR);
  thiosulfonic acid formation (TSAF);
  oxidative coupling (OC);
  ring closure (RC);
wherein these steps are completed in the same reaction vessel.

In some embodiments, the method of synthesis comprises the steps of, in order
  nitrosylation (NOS);
  nitrosyl reduction (NR);
  thiosulfonic acid formation (TSAF);
  oxidative coupling (OC);
  ring closure (RC);
wherein these steps are completed in the same reaction vessel.

In some embodiments, the NO, NR, TSAF and OC steps are completed in a first reaction vessel, the ring closure (RC) step is completed in a second reaction vessel, and salt formation (CSF) (and optionally recrystallisation (RX)) is completed in a third reaction vessel. In other words, this is a 'three pot' method.

In some embodiments, the NO, NR, TSAF, OC and RC steps are completed in a first reaction vessel, and salt formation (e.g. chloride salt formation CSF) (and optionally recrystallisation (RX)) is completed in a second pot. In other words, this is a 'two pot method'.

In a further aspect of the present invention, a method of synthesis is provided which comprises the steps of, in order
  thiosulfonic acid formation (TSAF);
  oxidative coupling (OC);
  ring closure (RC);
wherein during or prior to the thiosulfonic acid formation step (TSAF) an activating agent is added.

In some embodiments, the method of synthesis comprises the steps of, in order
  nitrosyl reduction (NR);
  thiosulfonic acid formation (TSAF);
  oxidative coupling (OC);
  ring closure (RC);
wherein during or prior to the thiosulfonic acid formation step (TSAF) an activating agent is added.

In some embodiments, the method of synthesis comprises the steps of, in order
  nitrosylation (NOS);
  nitrosyl reduction (NR);
  thiosulfonic acid formation (TSAF);
  oxidative coupling (OC);
  ring closure (RC);
wherein during or prior to the thiosulfonic acid formation step (TSAF) an activating agent is added.

In some embodiments, optionally, the Zwitterionic intermediate formed in the oxidative coupling step (OC) is isolated and purified, for example by filtration, before being subjected to the ring closure step (RC).

Optionally, in this aspect, the diaminophenothiazinium compound is not a $ZnCl_2$ double salt.

Nitrosylation (NOS)

In this step, an N,N-disubstituted-3-optionally substituted aniline, 1, is 4-nitrosylated to give an N,N-disubstituted-3-optionally substituted-4-nitrosyl aniline, 2, as illustrated in the following scheme:

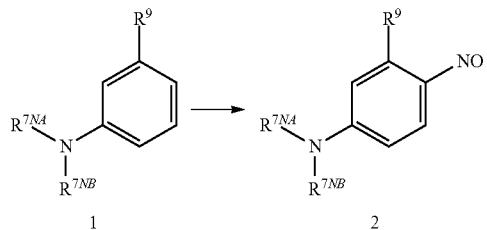

In some embodiments, an N,N-dimethyl aniline, 1', is 4-nitrosylated to give an N,N-dimethyl-4-nitrosyl aniline, 2', as illustrated in the following scheme:

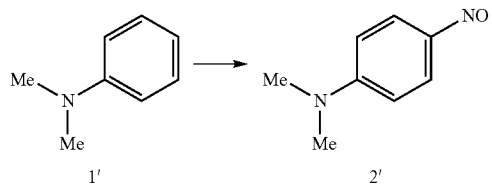

In some embodiments, the nitrosylation is performed using a nitrite.
In some embodiments, the nitrite is or comprises $NO_2^-$.
In some embodiments, the nitrite is or comprises alkali metal nitrite.
In some embodiments, the nitrite is or comprises sodium nitrite or potassium nitrite.
In some embodiments, the nitrite is sodium nitrite ($NaNO_2$).
In some embodiments, the molar ratio of nitrite to aniline, 1, is 0.8 to 1.5.
In some embodiments, the molar ratio is 1.0 to 1.5.
In some embodiments, the molar ratio is 1.1 to 1.5.
In some embodiments, the molar ratio is 1.1 to 1.3.
In some embodiments, the nitrosylation is performed under acidic conditions.
In some embodiments, the nitrosylation is performed at a pH of 1 or less.
In some embodiments, the nitrosylation is performed at a pH of 1 to −1.
In some embodiments, the nitrosylation is performed at a pH of 1 to 0.
(Unless otherwise specified, all pH values are measured at room temperature.)
In some embodiments, the acidic conditions are obtained using a strong acid.
In some embodiments, the acidic conditions are obtained using HCl (which has one strong acid proton).
In some embodiments, the molar ratio of acid protons to aniline, 1, is 1 to 4.
In some embodiments, the range is 2 to 4.
In some embodiments, the range is 3 to 4.
In some embodiments, the ratio is about 3.2.
In some embodiments, the range is 2 to 3.
In some embodiments, the range is 2.25 to 2.75.
In some embodiments, the ratio is about 2.5.
In some embodiments, the reaction is performed in an aqueous medium.
In some embodiments, the reaction temperature is 2 to 25° C.
In some embodiments, the reaction temperature is 2 to 15° C.
In some embodiments, the reaction temperature is 2 to 10° C.
In some embodiments, the reaction temperature is about 5° C.
In some embodiments, the reaction time is 10 to 240 minutes.
In some embodiments, the reaction time is 30 to 120 minutes.
In some embodiments, the reaction time is about 60 minutes.
In some embodiments, the reaction mixture is stirred during the reaction step.

Nitrosyl Reduction (NR)

In this step, an N,N-disubstituted-3-optionally substituted-4-nitrosyl aniline, 2, is reduced to form a N,N-disubstituted-1,4-diamino-5-optionally substituted benzene, 3, as illustrated in the following scheme:

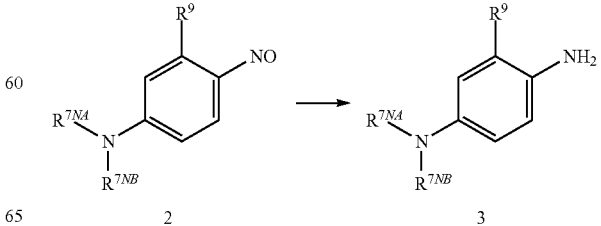

In some embodiments, an N,N-dimethyl-4-nitrosyl aniline, 2', is reduced to form a N,N-dimethyl-1,4-diaminobenzene, 3', as illustrated in the following scheme:

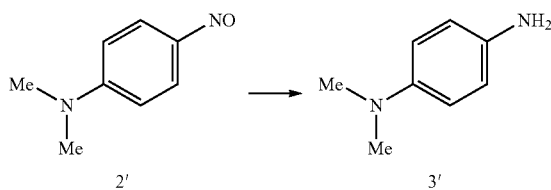

In some embodiments, the reduction is by reaction with a reducing agent.

In some embodiments, the reducing agent is or comprises Fe(0).

In some embodiments, the reducing agent is or comprises metallic iron.

In some embodiments, the reducing agent is metallic iron.

Metallic iron may be obtained commercially, for example, as metal filings.

In some embodiments, the molar ratio of Fe(0) to aniline, 1, is 1.0 to 4.0.

In some embodiments, the range is 1.5 to 4.0.
In some embodiments, the range is 1.5 to 3.0.
In some embodiments, the range is 1.5 to 2.5.
In some embodiments, the range is 1.5 to 3.5.
In some embodiments, the range is 2.0 to 3.0.
In some embodiments, the ratio is about 2.4.

In some embodiments, the excess of reducing agent used is sufficient to reduce any residual Cr(VI) from the subsequent oxidative coupling (OC) step.

In some embodiments, the reaction is performed under acidic conditions.

In some embodiments, the reaction is performed at a pH of 1 or less.

In some embodiments, the reaction is performed at a pH of 1 to −1.

In some embodiments, the reaction is performed at a pH of 1 to 0.

In some embodiments, the acidic conditions are obtained using a strong acid.

In some embodiments, the acidic conditions are obtained using HCl (which has one strong acid proton).

In some embodiments, the molar ratio of acid protons to aniline, 1, is 1 to 4.

In some embodiments, the range is 2 to 4.
In some embodiments, the range is 3 to 4.
In some embodiments, the ratio is about 3.2.
In some embodiments, the range is 2 to 3.
In some embodiments, the range is 2.25 to 2.75.
In some embodiments, the ratio is about 2.5

In some embodiments, the reaction is performed in an aqueous medium.

In some embodiments, the reaction is performed at a temperature of 2 to 35° C.

In some embodiments, the reaction is performed at a temperature of 10 to 30° C.

In some embodiments, the reaction is performed at a temperature of about 10° C.

In some embodiments, the reaction is performed for a time of 10 to 240 minutes.

In some embodiments, the reaction is performed for a time of 30 to 180 minutes.

In some embodiments, the reaction is performed for a time of about 120 minutes.

In some embodiments, the reaction mixture is stirred during the reaction step.

In contrast to the methods of WO2006/032879, when the reducing agent is metallic iron, excess metallic iron is not removed from the reaction mixture after reaction completion by filtration.

Thiosulfonic Acid Formation (TSAF)

In this step, an N,N-disubstituted-1,4-diamino-5-optionally substituted benzene, 3, is oxidized in the presence of a thiosulfate to give a thiosulfuric acid S-{2-(amino)-3-(optionally substituted)-5-(disubstituted-amino)-phenyl} ester, 4, as illustrated in the following scheme:

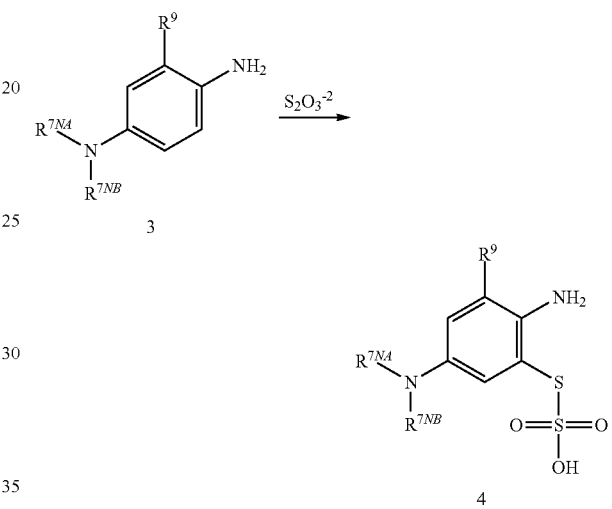

In some embodiments, an N,N-dimethyl-1,4-diaminobenzene, 3', is oxidized in the presence of a thiosulfate to give a thiosulfuric acid S-{2-(amino)-5-(dimethylamino)-phenyl} ester, 4', as illustrated in the following scheme:

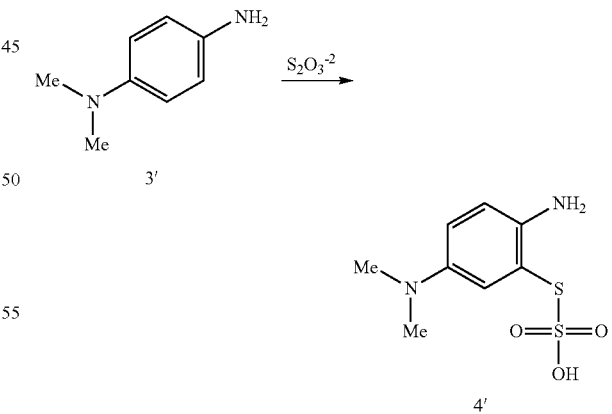

The thiosulfate is or comprises $S_2O_3^{-2}$.

In some embodiments, the thiosulfate is or comprises $Na_2S_2O_3$.

In some embodiments, the thiosulfate is $Na_2S_2O_3$ or a hydrate thereof.

$Na_2S_2O_3$ may be obtained commercially, for example, as the anhydrous salt or as the pentahydrate.

In some embodiments, the molar ratio of thiosulfate to diamine, 3, is 0.8 to 1.5.

In some embodiments, the molar ratio is 1.0 to 1.5.

In some embodiments, the molar ratio is 1.1 to 1.5.

In some embodiments, the molar ratio is 1.1 to 1.3.

In some embodiments, the oxidation is by reaction with an oxidizing agent.

In some embodiments, the oxidizing agent is or comprises Cr(VI).

In some embodiments, the oxidizing agent is or comprises $Cr_2O_7^{-2}$.

In some embodiments, the oxidizing agent is or comprises $Na_2Cr_2O_7$.

In some embodiments, the oxidizing agent is $Na_2Cr_2O_7$ or a hydrate thereof.

$Na_2Cr_2O_7$ may be obtained commercially, for example, as a dihydrate.

In some embodiments, the molar ratio of Cr(VI) to diamine, 3, is 0.2 to 2.0.

In some embodiments, the molar ratio is 0.2 to 1.0.

In some embodiments, the molar ratio is 0.2 to 0.8.

In some embodiments, the molar ratio is 0.3 to 0.7.

In some of the methods described herein, an activating agent may be added prior to or during the thiosulfonic acid formation step. This activates the thiosulfate ion, increasing its reactivity. The yield of the final diaminophenothiazinium compound is increased. In some cases, the yield increases by at least about 10%, preferably about 20%, and more preferably about 25%, relative to reactions in which the activating agent is omitted.

Without wishing to be bound by theory, it is thought that the activating agent promotes the nucleophilicity of the thiosulfate ion, thus increasing the yield of the thiosulfonic acid (in the TSAF step).

The activating agent may comprise or consists of a compound comprising an aluminium cation. The compound is preferably a water-soluble aluminium salt. The nature of the anion is not crucial, provided that it does not interfere with the reaction. Such compounds include, but are not limited to, aluminium sulphate. Without wishing to be bound by theory, it is thought that aluminium thiosulfate is so highly dissociated that it effectively reacts as a free thiosulfuric acid (see "The Fundamental Processes Of Dye Chemistry", by Dr. Hans Eduard Fierz-David).

For example, an activating agent consisting of aluminium sulphate hexadecahydrate may increase the yield by about 25%.

Between about 0.20 and about 2.0 molar equivalents of activating agent are preferably added to the mixture, relative to the number of moles of reagent starting materials (i.e. the N,N-dialkylaniline).

Accordingly, in some embodiments, the reaction is performed in the presence of an activating agent.

In some embodiments, the activating agent comprises Al(III).

In some embodiments, the activating agent comprises $Al_2(SO_4)_3$.

In some embodiments, the activating agent comprises a hydrate of $Al_2(SO_4)_3$.

In some embodiments, the activating agent comprises $Al_2(SO_4)_3$ hexadecahydrate.

In some embodiments, the molar ratio of Al(III) to the diamine is from about 0.05 to about 2.0

In some embodiments, the molar ratio of Al(III) to the diamine is from about 0.10 to about 2.0

In some embodiments, the molar ratio is from about 0.05 to about 1.0

In some embodiments, the molar ratio is from about 0.10 to about 1.0

In some embodiments, the molar ratio is from about 0.05 to about 0.8

In some embodiments, the molar ratio is from about 0.10 to about 0.8

In some embodiments, the molar ratio is from about 0.05 to about 0.6

In some embodiments, the molar ratio is from about 0.10 to about 0.6

In some embodiments, the molar ratio is from about 0.15 to about 0.5

In some embodiments, the molar ratio is about 0.15

In some embodiments, the molar ratio is about 0.5

In some embodiments, the reaction is performed in the presence of a strong acid.

Optionally, the acid may be added to the oxidising agent.

Alternatively, the acid may be added to the diamine before treatment with the oxidising agent.

In some embodiments, the strong acid is sulfuric acid ($H_2SO_4$) (which has two strong acid protons).

In some embodiments, the molar ratio of acid protons to diamine, 15, is 1.0 to 4.0.

In some embodiments, the range is 1.5 to 2.5.

In some embodiments, the range is about 2.0.

In some embodiments, the reaction is performed in an aqueous medium.

In some embodiments, the reaction temperature is 2 to 25° C.

In some embodiments, the reaction temperature is 2 to 15° C.

In some embodiments, the reaction temperature is 2 to 10° C.

In some embodiments, the reaction temperature is about 5° C.

In some embodiments, the reaction time is 10 to 240 minutes.

In some embodiments, the reaction time is 30 to 120 minutes.

In some embodiments, the reaction time is about 60 minutes.

In some embodiments, the reaction mixture is stirred during the reaction step.

Oxidative Coupling (OC)

In this step, a thiosulfuric acid S-{2-(amino)-3-(optionally substituted)-5-(disubstituted amino)-phenyl} ester, 4, is oxidatively coupled to an N,N-disubstituted-3-optionally substituted-aniline, 5, using an oxidizing agent that is or comprises Cr(VI), to give a [4-{2 (thiosulfate)-4-(disubstituted amino)-6-(optionally substituted)-phenyl-imino}-3-(optionally substituted)-cyclohexa-2,5-dienylidene]-N,N-disubstituted ammonium, 6, as illustrated in the following scheme:

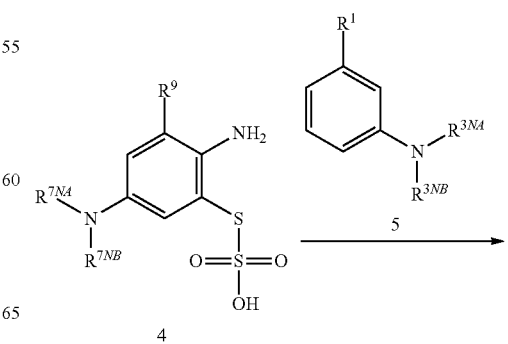

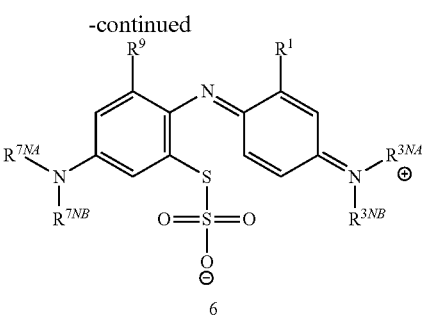

In some embodiments, a thiosulfuric acid S-{2-(amino)-5-(dimethylamino)-phenyl}ester, 4', is oxidatively coupled to an N,N-dimethyl-aniline, 5', using an oxidizing agent that is or comprises Cr(VI), to give a [4-{2 (thiosulfate)-4-(dimethylamino)-phenyl-imino}-cyclohexa-2,5-di-enylidene]-N,N-dimethyl ammonium, 6', as illustrated in the following scheme:

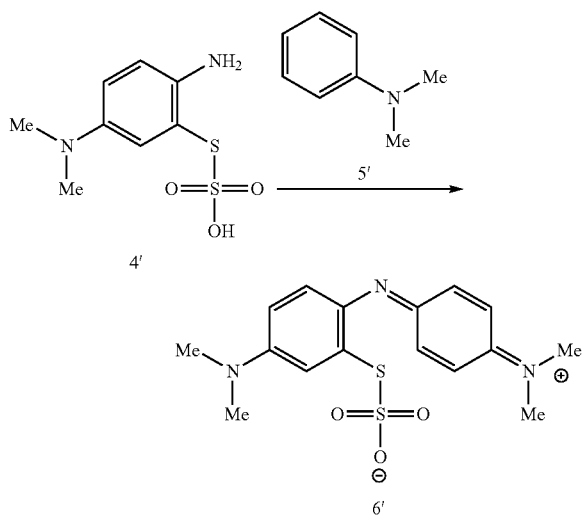

In some embodiments, the ester, 4, is added first, before the aniline, 5, is added.

In some embodiments, the oxidizing agent is or comprises $Cr_2O_7^{2-}$.

In some embodiments, the oxidizing agent is or comprises $Na_2Cr_2O_7$.

In some embodiments, the oxidizing agent is $Na_2Cr_2O_7$.

In some embodiments, the molar ratio of ester, 4, to aniline, 5, is 0.5 to 1.5.

In some embodiments, the range is 0.8 to 1.2.

In some embodiments, the range is about 1.0.

In some embodiments, the molar ratio of Cr(VI) to aniline, 5, is 0.4 to 4.0.

In some embodiments, the range is 0.6 to 3.0.

In some embodiments, the range is 0.8 to 3.0.

In some embodiments, the range is about 1.0.

In some embodiments, the reaction is performed under acidic conditions.

In some embodiments, the reaction is performed at a pH of 1 or less.

In some embodiments, the reaction is performed at a pH of 1 to −1.

In some embodiments, the reaction is performed at a pH of 1 to 0.

In some embodiments, the pH at the end of the reaction step, is 2 to 6.

In some embodiments, the pH at the end of the reaction step, is 3 to 5.

In some embodiments, the pH at the end of the reaction step, is about 4.

In some embodiments, the pH at the end of the reaction step, is about 3.94.

In some embodiments, the acidic conditions are obtained using a strong acid.

In some embodiments, the acidic conditions are obtained using $H_2SO_4$ (which has two strong acid protons).

In some embodiments, the molar ratio of acid protons to aniline, 5, is 1.0 to 4.0.

In some embodiments, the range is 1.5 to 2.5.

In some embodiments, the range is about 2.0.

In some embodiments, the reaction is performed in an aqueous medium.

In some embodiments, the reaction temperature is 2 to 20° C.

In some embodiments, the reaction temperature is 2 to 15° C.

In some embodiments, the reaction temperature is about 5° C.

In some embodiments, the reaction time is 10 minutes to 12 hours.

In some embodiments, the reaction time is 30 minutes to 4 hours.

In some embodiments, the reaction time is about 2 hours.

In some embodiments, the reaction mixture is stirred during the reaction step.

In some embodiments, aniline, 5, is the same as aniline, 1.

Isolation and Purification of Zwitterionic Intermediate (IAPOZI)

In this step, where present, the zwitterionic intermediate, 6, is isolated and purified.

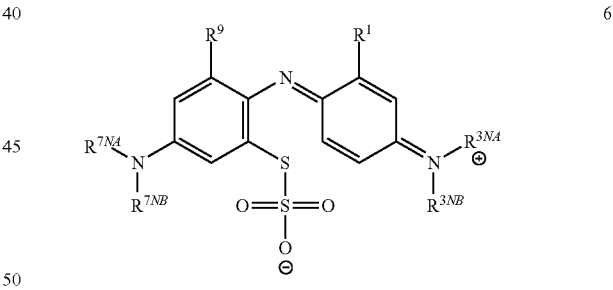

In some embodiments, the isolation and purification is by filtration.

In some embodiments, the isolation and purification is by filtration followed by washing.

In some embodiments, the washing is washing with $H_2O$.

In some embodiments, the washing is washing with $H_2O$ and tetrahydrofuran (THF).

In some embodiments, the volume ratio of $H_2O$ to THF is 1:1 to 10:1, preferably 4:1.

In some embodiments, the isolation and purification is by filtration followed by washing and drying.

In some embodiments, the drying is air-drying.

In some embodiments, the drying is air-drying for 2 to 72 hours.

In some embodiments, the drying is air-drying for 2 to 48 hours.

In some embodiments, the drying is air-drying for 2 to 24 hours.

In some embodiments, the drying is oven-drying.

In some embodiments, the drying is oven-drying for 2 to 72 hours.

In some embodiments, the drying is oven-drying for 2 to 48 hours.

In some embodiments, the drying is oven-drying for 2 to 24 hours.

In some embodiments, the drying is oven-drying at 30 to 60° C. for 2 to 48 hours.

For example, in some embodiments, the reaction mixture is filtered, and the residue (e.g., ~100 mmol crude product) is washed with $H_2O$ (e.g., 4×250 cm$^3$) and/or THF (e.g., 100 cm$^3$), and then air-dried overnight.

For example, in some embodiments, the reaction mixture is filtered (e.g., through a Buchner filter under vacuum), the solid removed, added to another vessel with fresh water, the mixture stirred vigorously, and filtered again. The "filter-recover-resuspend" process may be repeated a number of times. The finally obtained solid may be used in subsequent steps.

In some embodiments, a filter agent is added prior to filtration. This may improve the ease of filtration and reduce product loss in filtration.

A suitable filter agent comprises or consists of cellulose. Cellulose is a regenerative raw material, and thus can be disposed of by incineration while maintaining a closed CO2 cycle.

In some embodiments, filtration is followed by washing of the filtered product with a 'wash volume' of water.

In some such embodiments, the total wash volume is less than about 100 volumes (100 vol.) of water (relative to the amount of aniline), less than about 50 vol., less than about 30 vol., less than about 20 vol., or less than or about 10 vol.

In some embodiments, the total wash volume is used portionwise (for example, 4×10 vol. to give a total wash volume of 40 vol.).

It is noted that these wash volumes are significantly lower than the wash volumes used during filtrations in WO2006/032879.

The WO2006/032879 method uses approximately 250 volumes of water in total for the reaction. Using the methods of the present invention it is possible to reduce this to, for example, about 53 volumes of water.

Reduction in the wash volume reduces the water waste at the end of the reaction and is advantageous as it significantly reduces the waste volume. Smaller waste volumes have the advantage of easier storage and transport, and may therefore represent a cost saving. Additionally, a smaller wash volume means the filtration regime will be shorter overall, with consequent time and energy savings. Additionally, since the wash volumes may be heated for this procedure, a smaller overall volume has additional advantages in terms of energy and cost savings.

In some embodiments, the filtered residue is used directly in the next step without further treatment.

Ring Closure (RC)

In this step, a [4-{2 (thiosulfate)-4-(disubstituted amino)-6-(optionally substituted)-phenyl-imino}-3-(optionally substituted)-cyclohexa-2,5-dienylidene]-N,N-disubstituted ammonium, 6, is subjected to ring closure to give a 3,7-bis(disubstituted-amino)-1,9-(optionally substituted)-phenothiazin-5-ium salt, 7, as illustrated in the following scheme:

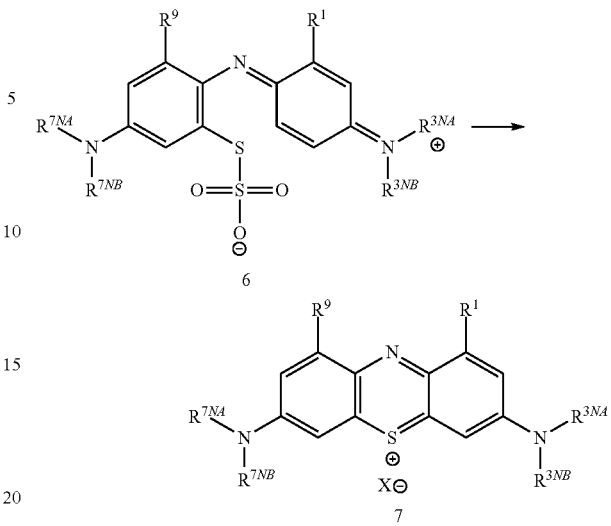

In some embodiments, a [{2-(thiosulfate)-4-(dimethylamino)-phenyl-imino}-cyclohexa-2,5-dienylidene]-N,N-dimethyl ammonium, 6', is subjected to ring closure to give a 3,7-bis(dimethylamino)-phenothiazin-5-ium salt, 7', as illustrated in the following scheme:

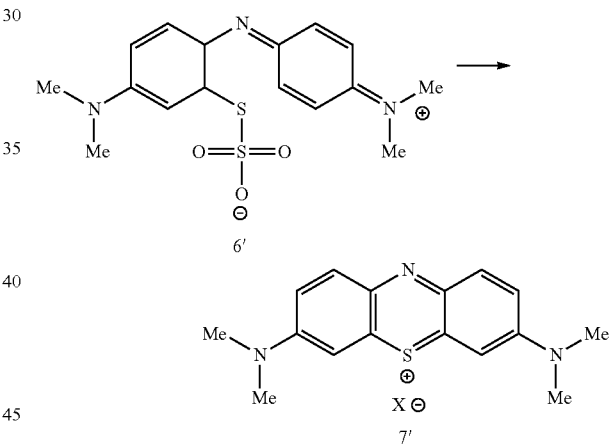

In some embodiments, ring closure is achieved by treatment with an oxidizing agent.

In some embodiments, the oxidizing agent is or comprises Cu(II).

In some embodiments, the oxidizing agent is or comprises Cu(II) sulfate.

In some embodiments, the oxidizing agent is Cu(II) sulfate or a hydrate thereof.

Cu(II) sulfate may be obtained commercially, for example, as a pentahydrate.

Without wishing to be bound by any particular theory, it is believed that the Cu(II) is converted to Cu(I) in the reaction, and precipitates as insoluble $Cu_2O$.

In some embodiments, ring closure is performed under acidic conditions.

In some embodiments, ring closure is performed at a pH of 1 to 5.

In some embodiments, ring closure is performed at a pH of 2 to 5.

In some embodiments, ring closure is performed at a pH of 3 to 4.5.

In some embodiments, ring closure is performed at a pH of 3.5 to 4.1.

In some embodiments, ring closure is performed at a pH of about 3.8.

In some embodiments, the desired pH is obtained by the addition of strong acid.

In some embodiments, the desired pH is obtained by the addition of HCl.

In some embodiments, the molar ratio of Cu(II) to ammonium, 6, is 0.02 to 0.15.

In some embodiments, the range is 0.03 to 0.12

In some embodiments, the range is about 0.10.

In some embodiments, the reaction is performed in an aqueous medium.

In some embodiments, the reaction is performed by slurrying the [4-{2 (thiosulfate)-4-(disubstituted amino)-6-(optionally substituted)-phenyl-imino}-3-(optionally substituted)-cyclohexa-2,5-dienylidene]-N,N-disubstituted ammonium, 6 (e.g. as obtained from the oxidative coupling (OC) step) in an aqueous hydrochloric acid solution, adding the oxidising agent, and then heating.

In some such embodiments, the slurry volume used is from about 15 to about 30 volumetric equivalents (15 vol. to 30 vol.), relative to the aniline i.e. for 10.0 g of aniline (approximately 10 mL) the slurry volume would be from about 150 to 300 mL.

In some embodiments, the slurry volume is about 25 vol.

This slurry volume is significantly reduced compared to the slurry volume used in the WO2006/032879 method. Without wishing to be bound by theory, it is thought that the significant reduction of the slurry volume used in this step may be advantageous for a number of reasons. Firstly, it has the benefit of a reduced reactor capacity being required, meaning either a smaller reactor vessel is required for synthesis using the same mass of Bindschedler's Green intermediate, or a larger mass could be used in the standard size of vessel used. This may have benefits in terms of throughput. Secondly, the ring closure step takes place at elevated temperature (85° C.), thus a smaller solvent volume may be advantageous since it will take a shorter time to reach optimum temperature, and require less energy input to reach that temperature, resulting in both energy and cost savings. Use of a smaller slurry volume may also lead to an increase in product yield. The cost of waste disposal, treatment and transport is also reduced if a smaller volume of effluent is finally obtained at the end of the process.

In some embodiments, the reaction temperature is 30 to 95° C.

In some embodiments, the reaction temperature is 50 to 90° C.

In some embodiments, the reaction temperature is 60 to 90° C.

In some embodiments, the reaction temperature is about 85° C.

In some embodiments, the reaction time is 10 to 120 minutes.

In some embodiments, the reaction time is 20 to 90 minutes.

In some embodiments, the reaction time is about 60 minutes.

In some embodiments, the reaction is performed until the reaction mixture changes colour, e.g., becomes a deep blue colour.

In some embodiments, the reaction mixture is stirred during the reaction step.

In some embodiments, after reaction, the reaction mixture is filtered and the filtrate collected. (The filtrate contains the desired product in solution.)

In some embodiments, the filtration is performed at a temperature near to the reaction temperature, to give a "hot" filtrate.

In some embodiments, the reaction mixture is first cooled, and the filtration is performed at about room temperature, to give a "cool" filtrate.

In some embodiments, a filter agent is added prior to filtration. This may improve the ease of filtration and reduce product loss in filtration.

A suitable filter agent comprises or consists of cellulose. Cellulose is a regenerative raw material, and thus can be disposed of by incineration while maintaining a closed $CO_2$ cycle.

In some embodiments, filtration is followed by washing of the filtered product with a 'wash volume' of water.

In some such embodiments, the total wash volume is less than about 200 volumes (200 vol.) of water (relative to the amount of aniline), less than about 150 vol., less than about 100 vol., less than about 50 vol., less than about 25 vol., or less than or about 20 vol.

In some embodiments, the total wash volume is used portionwise (e.g. 4×10 vol. to give a total wash volume of 40 vol., or 4×5 vol. to give a total wash volume of 20 vol.).

It is noted that these wash volumes are significantly lower than the wash volumes used during filtrations in WO2006/032879.

As mentioned above, the WO2006/032879 method uses approximately 250 volumes of water in total for the reaction. Using the methods of the present invention it is possible to reduce this to, for example, about 53 volumes of water.

Reduction in the wash volume reduces the water waste at the end of the reaction and is advantageous as it significantly reduces the waste volume. Smaller waste volumes have the advantage of easier storage and transport, and may therefore represent a cost saving. Additionally, a smaller wash volume means the filtration regime will be shorter overall, with consequent time and energy savings. Additionally, since the wash volumes may be heated for this procedure, a smaller overall volume has additional advantages in terms of energy and cost savings.

Advantageously, in some embodiments, the final waste filtrate obtained after the above-described filtration can, with adjustment to the relevant pH, be used as the slurry solvent for this step in subsequent reactions for at least 2 reaction cycles. This is advantageous since it allows for recycling of what is a waste product, but also leads to higher yields of product.

Chloride Salt Formation (CSF)

In this step, a 3,7-bis(disubstituted-amino)-1,9-(optionally substituted)-phenothiazin-5-ium salt, 7, is reacted with chloride, to give a 3,7-bis(disubstituted-amino)-1,9-(optionally substituted)-phenothiazin-5-ium chloride salt, 8, as illustrated in the following scheme:

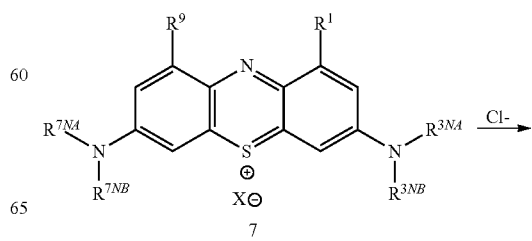

7

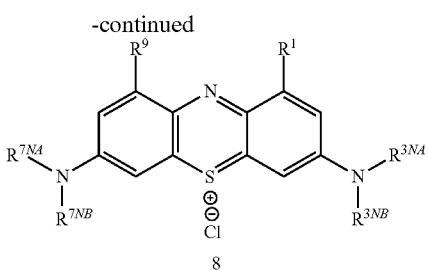

In some embodiments, a 3,7-bis(dimethylamino)-phenothiazin-5-ium salt, 7', is reacted with chloride, to give a 3,7-bis(dimethylamino)-phenothiazin-5-ium chloride salt, 8' (i.e., MTC), as illustrated in the following scheme:

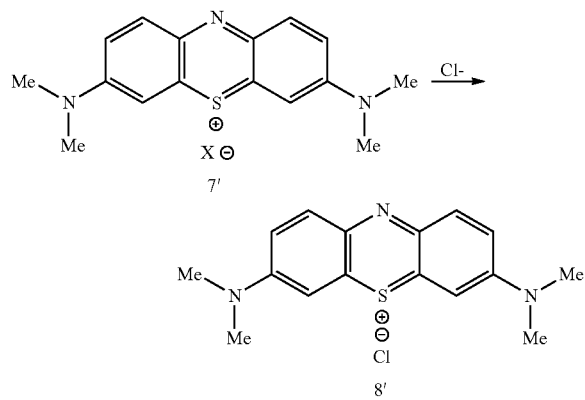

Treatment with Hydrochloric Acid as a Source of Chloride:

In some embodiments, the chloride is hydrochloric acid.

In some embodiments, the reaction is performed at a relatively low pH.

In some embodiments, the relatively low pH is −1 to 3.
In some embodiments, the relatively low pH is 0 to 3.
In some embodiments, the relatively low pH is 0 to 2.
In some embodiments, the relatively low pH is about 1.
In some embodiments, the pH is adjusted to the relatively low pH slowly.
In some embodiments, the pH is adjusted over a period of 5 to 120 minutes.
In some embodiments, the pH is adjusted over a period of 5 to 60 minutes.
In some embodiments, the pH is adjusted over a period of 5 to 30 minutes.
In some embodiments, the pH is adjusted over a period of about 10 minutes.

In some embodiments, the reaction is performed at a relatively cool temperature.

In some embodiments, the relatively cool temperature is 2 to 40° C.
In some embodiments, the relatively cool temperature is 2 to 30° C.
In some embodiments, the relatively cool temperature is 5 to 30° C.
In some embodiments, the relatively cool temperature is 10 to 30° C.
In some embodiments, the relatively cool temperature is 15 to 30° C.
In some embodiments, the relatively cool temperature is 20 to 30° C.

In some embodiments, the relatively cool temperature is about 25° C.

In some embodiments, the reaction is performed until the reaction mixture (initially, e.g., a deep blue colour) becomes light blue to colourless.

In some embodiments, the reaction mixture is stirred during the reaction step.

Treatment with a Chloride Salt as a Source of Chloride:

In some embodiments, the chloride is chloride salt.
In some embodiments, the chloride is alkali metal chloride.
In some embodiments, the chloride is sodium chloride.
In some embodiments, there is a large molar excess of (sodium) chloride.
In some embodiments, the molar ratio of chloride to salt, 7, is 5 to 200.
In some embodiments, the molar ratio is 10 to 150.
In some embodiments, the molar ratio is 10 to 100.
In some embodiments, the molar ratio is about 50.

In some embodiments, the reaction is performed in an aqueous medium.

In some embodiments, the reaction temperature is 20 to 95° C.
In some embodiments, the reaction temperature is 30 to 95° C.
In some embodiments, the reaction temperature is 50 to 80° C.
In some embodiments, the reaction temperature is about 65° C.
In some embodiments, the reaction temperature is about room temperature.

In some embodiments, the reaction time is 10 to 30 minutes.

In some embodiments, the reaction is performed until the reaction mixture (initially, e.g., a deep blue colour) becomes light blue to colourless.

In some embodiments, the reaction mixture is stirred during the reaction step.

In some embodiments, the reaction mixture is allowed to cool following addition of the chloride, to yield the product as a precipitate.

In some embodiments, the final diaminophenothiazinium compound is washed with aqueous acid after precipitation/crystallization.

Without wishing to be bound by theory, this additional acid wash may help to remove inorganic salt contaminants and so may result in a purer diaminophenothiazinium product. The acid wash 'de-liquors' the diaminophenothiazinium product when it is on the filter, thus removing the residual reaction medium, which may contain high levels of salts and other impurities.

In some embodiments, the acid wash is performed with aqueous hydrochloric acid solution.
In some embodiments, the acid wash is performed with 5% aqueous hydrochloric acid solution.
In some embodiments, the acid wash is performed with aqueous hydrochloric acid solution.
In some embodiments, the acid wash is performed with from about 1 to about 3 volumes (1 vol. to 3 vol.) of the aqueous acid solution.
In some embodiments, the acid wash is performed with about 2 volumes (2 vol.) of aqueous acid solution.
In some embodiments, the acid wash is performed with 2×1 vol. of the aqueous acid solution.

Following the chloride salt formation (CSF) step, one or more additional treatment or purification steps (i.e., ST, DT, CT, EDTAT, OE) may be performed, as described further below. If two or more of these treatment steps are performed, they may be performed in any order. These treatment steps give rise to improved purity, especially reduced metal content and reduced organic impurity content.

Additional Treatment

In some embodiments, the method of synthesis additionally comprises a subsequent step selected from:
- sulphide treatment (ST);
- dimethyldithiocarbamate treatment (DT);
- carbonate treatment (CT); and
- ethylenediaminetetraacetic acid treatment (EDTAT).

In some embodiments, the method of synthesis additionally comprises a subsequent step selected from:
- sulphide treatment (ST);
- dimethyldithiocarbamate treatment (DT);
- carbonate treatment (CT);
- ethylenediaminetetraacetic acid treatment (EDTAT); and
- organic extraction (OE).

In some embodiments, the method of synthesis additionally comprises a subsequent step selected from:
- sulphide treatment (ST);
- dimethyldithiocarbamate treatment (DT);
- carbonate treatment (CT); and
- ethylenediaminetetraacetic acid treatment (EDTAT);

followed by the subsequent step of:
- organic extraction (OE).

In some embodiments, the method of synthesis additionally comprises a subsequent step selected from:
- sulphide treatment (ST);

followed by the subsequent step of:
- organic extraction (OE).

In some embodiments, the method of synthesis additionally comprises the subsequent step of:
- organic extraction (OE).

In some embodiments, the method of synthesis additionally comprises the subsequent step of:
- recrystallisation (RX).

Thus, In some embodiments, the method of synthesis comprises the steps of, in order:
- nitrosylation (NOS);
- nitrosyl reduction (NR);
- thiosulfonic acid formation (TSAF);
- oxidative coupling (OC);
- optionally, isolation and purification of zwitterionic intermediate (IAPOZI);
- ring closure (RC);
- chloride salt formation (CSF);
- one or more of:
- sulphide treatment (ST);
- dimethyldithiocarbamate treatment (DT);
- carbonate treatment (CT); and
- ethylenediaminetetraacetic acid treatment (EDTAT);
- organic extraction (OE);
- recrystallisation (RX).

In some embodiments, one or more additional treatment steps selected from ST, DT, CT, and EDTAT are performed, followed by OE.

Sulphide Treatment (ST)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is treated with a sulphide.

In some embodiments, the salt, 7, is treated with a sulphide.

In some embodiments, the chloride salt, 8, is treated with a sulphide.

The sulphide is or comprises $S^{2-}$.

In some embodiments, the sulphide is a metal sulphide.
In some embodiments, the sulphide is an alkali metal sulphide.
In some embodiments, the sulphide is or comprises $Na_2S$.
In some embodiments, the sulphide is $Na_2S$.
In some embodiments, the sulphide is a transition metal sulphide.
In some embodiments, the sulphide is or comprises ZnS.
In some embodiments, the sulphide is ZnS.
In some embodiments, the amount of sulphide is 0.01 to 0.20 equivalents.
In some embodiments, the range is 0.05 to 0.15 equivalents.
In some embodiments, the range is about 0.1 equivalents.
In some embodiments, the (initial) concentration of salt 7 or 8 is 0.005 to 0.25 M.
In some embodiments, range is 0.02 to 0.30 M.
In some embodiments, range is 0.05 to 0.20 M.
In some embodiments, the (initial) concentration is about 0.10 M.
In some embodiments, the treatment is treatment with a sulphide and a chloride.
In some embodiments, the chloride is or comprises NaCl.
In some embodiments, the chloride is NaCl.
In some embodiments, there is a molar excess of chloride.
In some embodiments, the amount of chloride is 5 to 300 equivalents.
In some embodiments, the amount of chloride is 5 to 40 equivalents.
In some embodiments, the amount of chloride is 5 to 30 equivalents.
In some embodiments, the amount of chloride is about 20 equivalents.
In some embodiments, the amount of chloride is about 200 equivalents.
In some embodiments, the treatment is performed at a temperature of 2 to 20° C.
In some embodiments, the temperature range is 2 to 15° C.
In some embodiments, the temperature range is 5 to 15° C.
In some embodiments, the temperature is about 10° C. (e.g., 10±2° C.).
In some embodiments, the treatment is performed in an aqueous medium.
In some embodiments, the treatment is performed under basic conditions.
In some embodiments, the treatment is performed at a pH of 9 to 12.
In some embodiments, the treatment is performed at a pH of 10 to 11.
In some embodiments, the treatment is performed at a pH of about 10.5.
In some embodiments, the treatment is performed so that the pH of the reaction mixture reaches at least 9 to 12.
In some embodiments, the treatment is performed so that the pH of the reaction mixture reaches at least 10 to 11.
In some embodiments, the treatment is performed so that the pH of the reaction mixture reaches at least about 10.5.
In some embodiments, the treatment is performed at a temperature of about 10° C. (e.g., 10±2° C.) and at a pH of about 10.5, or is performed so that the pH of the reaction mixture reaches at least about 10.5.
In some embodiments, the reaction mixture is stirred during the reaction step.
For example, In some embodiments, crude MTC product is fully dissolved in water at a concentration of about 0.1 M at a temperature of about 65° C. The solution is cooled. The cooled solution is optionally filtered. The solution is treated with about 0.1 equivalents of aqueous sodium sulphide, or an amount sufficient to achieve a pH of about 10.5 (e.g., 10.5±0.5). The resulting mixture is stirred (e.g., for about 10 minutes), filtered, and the filtrate collected. In some embodiments, a large excess of sodium chloride (e.g., about 23 equivalents) is added to the filtrate with stirring, and the resulting precipitate is collected. Alternatively, in another embodiment, the pH of the cool (e.g., about 20° C.) solution is adjusted to about pH 1 using HCl, and the resulting precipitate collected.

In some embodiments, following treatment with sulphide (e.g., and before treatment with chloride), the product (e.g., in solution) is additionally washed with an organic solvent.

In some embodiments, the organic solvent is selected from dichloromethane, 1,2-dichloroethane, chloroform, ethyl acetate, diethyl ether, chlorobenzene, petroleum ether (e.g., 40:60), benzene, toluene, and methyl acetate. In some embodiments, the organic solvent is dichloromethane.

In some embodiments, e.g., following washing with an organic solvent, the pH of the solution of the washed product is adjusted to about 4.5 to about 5.5, or about 5.0. In some embodiments, the solution is (e.g., is additionally) heated/cooled to approximately 20° C. and then subjected to cool acid recrystallisation (e.g., pH adjusted to about 1 using HCl, and the resulting precipitate collected). In an alternative embodiment, the solution is (e.g., is additionally) heated to approximately 65° C. and subjected to hot salting out.

For example, In some embodiments, crude MTC product is fully dissolved in water at a concentration of about 0.06 M at a temperature of about 60° C. The solution is cooled. The cooled solution is optionally filtered. The solution is treated with about 0.07 equivalents of aqueous sodium sulphide. The resulting mixture is stirred (e.g., for about 15 minutes), filtered, and the filtrate collected. The filtrate is washed with dichloromethane (e.g., several times). In some embodiments, the washed filtrate is heated to about 60° C., and a large excess of sodium chloride (e.g., about 260 equivalents) is added to the (hot) filtrate with stirring. The hot solution is allowed to cool very slowly, and the (highly crystalline) precipitate is collected (e.g., "hot salting out"). Alternatively, in another embodiment, the pH of the cool (e.g., about 20° C.) washed filtrate is adjusted to about pH 1 using HCl, and the resulting precipitate collected.

Dimethyldithiocarbamate Treatment (DT)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is treated with a dimethyldithiocarbamate.

In some embodiments, the salt, 7, is treated with a dimethyldithiocarbamate.

In some embodiments, the chloride salt, 8, is treated with a dimethyldithiocarbamate.

The dimethyldithiocarbamate is or comprises $(CH_3)_2NCS_2^-$.

In some embodiments, the dimethyldithiocarbamate is or comprises $(CH_3)_2NCS_2Na$.

In some embodiments, the dimethyldithiocarbamate is $(CH_3)_2NCS_2Na$.

In some embodiments, the amount of dimethyldithiocarbamate is 0.01 to 0.20 equivalents.

In some embodiments, the range is 0.05 to 0.15 equivalents.

In some embodiments, the range is about 0.1 equivalents.

In some embodiments, the (initial) concentration of salt 7 or 8 is 0.005 to 0.25 M.

In some embodiments, range is 0.02 to 0.30 M.

In some embodiments, range is 0.05 to 0.20 M.

In some embodiments, the (initial) concentration is about 0.10 M.

In some embodiments, the treatment is treatment with a dimethyldithiocarbamate and a chloride.

In some embodiments, the chloride is or comprises NaCl.

In some embodiments, the chloride is NaCl.

In some embodiments, there is a molar excess of chloride.

In some embodiments, the amount of chloride is 5 to 40 equivalents.

In some embodiments, the amount of chloride is 5 to 30 equivalents.

In some embodiments, the amount of chloride is about 20 equivalents.

In some embodiments, the treatment is performed in an aqueous medium.

In some embodiments, the reaction mixture is stirred during the reaction step.

For example, in some embodiments, crude MTC product is fully dissolved in water at a concentration of about 0.1 M at a temperature of about 65° C. The solution is cooled. The cooled solution is optionally filtered. The solution is treated with about 0.1 equivalents of aqueous dimethyldithiocarbamic acid, sodium salt. The resulting mixture is stirred (e.g., for about 10 minutes), filtered, and the filtrate collected. A large excess of sodium chloride (e.g., about 23 equivalents) is added to the filtrate with stirring, and the resulting precipitate is collected.

In some embodiments, following treatment with dimethyldithiocarbamate (e.g., and before treatment with chloride), the product (e.g., in solution) is additionally washed with an organic solvent, as described above for sulphide treatment.

In some embodiments, e.g., following washing with an organic solvent, the pH of the solution of the washed product is adjusted to about 4.5 to about 5.5, or about 5.0, as described above for sulphide treatment.

Carbonate Treatment (CT)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is treated with a carbonate.

In some embodiments, the salt, 7, is treated with a carbonate.

In some embodiments, the chloride salt, 8, is treated with a carbonate.

The carbonate is or comprises $CO_3^{2-}$.

In some embodiments, the carbonate is or comprises alkali metal carbonate.

In some embodiments, the carbonate is or comprises sodium carbonate.

In some embodiments, the carbonate is sodium carbonate.

In some embodiments, the amount of sodium carbonate is 0.01 to 0.20 equivalents.

In some embodiments, the range is 0.05 to 0.15 equivalents.

In some embodiments, the amount is about 0.1 equivalents.

In some embodiments, the (initial) concentration of salt 7 or 8 is 0.005 to 0.25 M.

In some embodiments, range is 0.02 to 0.30 M.

In some embodiments, range is 0.05 to 0.20 M.

In some embodiments, the (initial) concentration is about 0.10 M.

In some embodiments, the treatment is treatment with a carbonate and a chloride.

In some embodiments, the chloride is or comprises NaCl.

In some embodiments, the chloride is NaCl.

In some embodiments, there is a molar excess of chloride.

In some embodiments, the amount of chloride is 5 to 40 equivalents.

In some embodiments, the amount of chloride is 5 to 30 equivalents.

In some embodiments, the amount of chloride is about 20 equivalents.

In some embodiments, the treatment is performed in an aqueous medium.

In some embodiments, the reaction mixture is stirred during the reaction step.

For example, In some embodiments, crude MTC product is fully dissolved in water at a concentration of about 0.1 M at a temperature of about 65° C. The solution is cooled. The cooled solution is optionally filtered. The solution is treated with about 0.1 equivalents of aqueous sodium carbonate. The resulting mixture is stirred (e.g., for about 10 minutes), filtered, and the filtrate collected. A large excess of sodium chloride (e.g., about 23 equivalents) is added to the filtrate with stirring, and the resulting precipitate is collected.

In some embodiments, following treatment with carbonate (e.g., and before treatment with chloride), the product (e.g., in solution) is additionally washed with an organic solvent, as described above for sulphide treatment.

In some embodiments, e.g., following washing with an organic solvent, the pH of the solution of the washed product is adjusted to about 4.5 to about 5.5, or about 5.0, as described above for sulphide treatment.

Ethylenediaminetetraacetic Acid Treatment (EDTAT)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, is treated with ethylenediaminetetraacetic acid (EDTA) or an EDTA salt.

In some embodiments, the salt, 7, is treated with EDTA or an EDTA salt.

In some embodiments, the chloride salt, 8, is treated with EDTA or an EDTA salt.

In some embodiments, the EDTA salt is or comprises EDTA alkali metal salt.

In some embodiments, the EDTA salt is or comprises EDTA disodium salt.

In some embodiments, the EDTA salt is EDTA disodium salt.

In some embodiments, the amount of EDTA is 0.01 to 0.20 equivalents.

In some embodiments, the range is 0.05 to 0.15 equivalents.

In some embodiments, the amount is about 0.1 equivalents.

In some embodiments, the (initial) concentration of salt 7 or 8 is 0.005 to 0.25 M.

In some embodiments, range is 0.02 to 0.30 M.

In some embodiments, range is 0.05 to 0.20 M.

In some embodiments, the (initial) concentration is about 0.10 M.

In some embodiments, the treatment is treatment with EDTA or an EDTA salt and a chloride.

In some embodiments, the chloride is or comprises NaCl.

In some embodiments, the chloride is NaCl.

In some embodiments, there is a molar excess of chloride.

In some embodiments, the amount of chloride is 5 to 40 equivalents.

In some embodiments, the amount of chloride is 5 to 30 equivalents.

In some embodiments, the amount of chloride is about 10 equivalents.

In some embodiments, the treatment is performed in an aqueous medium.

In some embodiments, the reaction mixture is stirred during the reaction step.

For example, In some embodiments, crude MTC product is fully dissolved in water at a concentration of about 0.1 M at a temperature of about 65° C. The solution is cooled to room temperature, and then the solution is treated with about 0.1 equivalents of aqueous EDTA disodium salt. The resulting mixture is stirred (e.g., for about 1 hour), filtered, and the filtrate collected. A large excess of sodium chloride (e.g., about 10 equivalents) is added to the filtrate with stirring, and the resulting precipitate is collected.

In some embodiments, following treatment with EDTA (e.g., and before treatment with chloride), the product (e.g., in solution) is additionally washed with an organic solvent, as described above for sulphide treatment.

In some embodiments, e.g., following washing with an organic solvent, the pH of the solution of the washed product is adjusted to about 4.5 to about 5.5, or about 5.0, as described above for sulphide treatment.

Organic Extraction (OE)

In this step, a 3,7-bis(disubstituted-amino)-1,9-(optionally substituted)-phenothiazin-5-ium salt, 7, or a 3,7-bis(disubstituted-amino)-1,9-(optionally substituted)-phenothiazin-5-ium chloride salt, 8, in aqueous solution or suspension, is treated with (e.g., washed with) an organic solvent.

In some embodiments, the salt, 7, in aqueous solution or suspension, is treated with (e.g., washed with) an organic solvent.

In some embodiments, the chloride salt, 8, in aqueous solution or suspension, is treated with (e.g., washed with) an organic solvent.

In some embodiments, the organic solvent is dichloromethane ($CH_2Cl_2$, DCM).

DCM is a "class 2" chemical, with a permitted daily exposure (PDE) of 6 mg/day.

In some embodiments, the volume ratio of aqueous solution or suspension of salt, 7 or 8, to organic solvent (e.g., DCM) is 0.1 to 10.

In some embodiments, the ratio is 0.5 to 5.

In some embodiments, the ration is 0.5 to 2.

In some embodiments, the treatment (e.g., washing) is performed iteratively using a plurality of aliquots of the organic solvent (e.g., DCM).

For example, In some embodiments, 250 mL of aqueous solution of the salt, 7 or 8, is washed with 50 mL of DCM, five times, for a total volume of 250 mL DCM, and a volume ratio of 1.

In some embodiments, aqueous solution or suspension of salt, 7 or 8, has a pH of 8 to 12.

In some embodiments, the pH range is 9 to 12.

In some embodiments, the pH range is 9 to 11.

In some embodiments, the pH range is about 10.8.

In some embodiments, the treatment (e.g., washing) is performed at a temperature of 2 to 20° C.

In some embodiments, the temperature range is 2 to 15° C.

In some embodiments, the temperature is about 10° C.

Treatment (e.g., washing) may be performed, for example, using a reaction vessel equipped with an overhead mechanical stirrer attached to a shaft with a paddle as well as a run-off tap at the bottom of the flask. Aqueous solution or suspension of salt, 7 or 8, is placed in the vessel, and an aliquot of organic solvent (e.g., DCM) is added and the heterogeneous mixture stirred for a suitable period. The layers are allowed to separate, and the lower (organic solvent) layer is discarded via the run-off tap. Another aliquot of organic solvent (e.g., DCM) is added and the process repeated, e.g., several times.

Organic extraction (OE) is particularly effective at greatly reducing the organic impurity levels of the solid (e.g., crystalline) product ultimately obtained.

In some embodiments, one or more additional treatment steps selected from ST, DT, CT, and EDTAT are performed first, followed by organic extraction (OE).

Recrystallisation (RX)

In this step, a 3,7-bis(disubstituted-amino)-1,9-(optionally substituted)-phenothiazin-5-ium salt, 7, or a 3,7-bis (disubstituted-amino)-1,9-(optionally substituted)-phenothiazin-5-ium chloride salt, 8, is recrystallised.

In some embodiments, the salt, 7, is recrystallised.

In some embodiments, the chloride salt, 8, is recrystallised.

The recrystallisation step further improves purity and also provides a product with a suitable particle size, e.g., a particle size suitable for use in subsequent pharmaceutical formulation.

For the avoidance of doubt, note that "crystallisation" and "recrystallisation" are used interchangeably herein to mean the formation of a solid precipitate (e.g., crystals) from a solution or suspension, and that "re-" in the term "recrystallisation" does not require that the newly crystallised product was previously in a solid or crystalline form.

In some embodiments, after recrystallisation, the crystalline product is filtered and then washed on the filter with a wash solution.

In some embodiments, the wash solution is a dilute aqueous acid.

In some embodiments, the wash solution is chilled, acidified, water.

In some embodiments, the wash solution is at a pH of about 1.

In some embodiments, the wash solution is at a temperature of about 5° C.

In some embodiments, washing is performed with from about 1 to about 5 volumes (1 vol. to 5 vol.) of the wash solution.

In some embodiments, the acid wash is performed with about 4 volumes (4 vol.) of the ash solution.

In some embodiments, the acid wash is performed with 2×4 vol. of the wash solution.

Cool Acidic Recrystallisation (RX-CAR):

In some embodiments, the recrystallisation is recrystallisation from water (e.g., from an aqueous solution or aqueous suspension) at a relatively cool temperature by adjusting the pH to a relatively low pH (e.g., "cool acidic crystallisation").

In some embodiments, the pH is adjusted using HCl.

In some embodiments, the relatively cool temperature is 2 to 40° C.

In some embodiments, the relatively cool temperature is 2 to 30° C.

In some embodiments, the relatively cool temperature is 5 to 30° C.

In some embodiments, the relatively cool temperature is 10 to 30° C.

In some embodiments, the relatively cool temperature is 15 to 30° C.

In some embodiments, the relatively cool temperature is 20 to 30° C.

In some embodiments, the relatively cool temperature is about 25° C.

In some embodiments, the relatively low pH is −1 to 3.

In some embodiments, the relatively low pH is 0 to 3.

In some embodiments, the relatively low pH is 0 to 2.

In some embodiments, the relatively low pH is about 1.

In some embodiments, the pH is adjusted to the relatively low pH slowly.

In some embodiments, the pH is adjusted over a period of 5 to 120 minutes.

In some embodiments, the pH is adjusted over a period of 5 to 60 minutes.

In some embodiments, the pH is adjusted over a period of 5 to 30 minutes.

In some embodiments, the pH is adjusted over a period of about 10 minutes.

Cool acidic recrystallisation (RX-CAR) is particularly effective at greatly reducing the metal content of the results solid (e.g., crystalline) product.

Hot Salting Out (RX-HSO):

In some embodiments, the recrystallisation is recrystallisation from water (e.g., from an aqueous solution or aqueous suspension) at an initial elevated temperature, in the presence of a chloride, such as sodium chloride (e.g., "hot salting out").

In some embodiments, the (initial) concentration of salt 7 or 8 is 0.002 to 0.05 M.

In some embodiments, range is 0.005 to 0.04 M.

In some embodiments, range is 0.01 to 0.04 M.

In some embodiments, the (initial) concentration is about 0.03 M.

In some embodiments, the initial elevated temperature is 30 to 90° C.

In some embodiments, the range is 40 to 80° C.

In some embodiments, the range is 50 to 80° C.

In some embodiments, the initial elevated temperature is about 65° C.

In some embodiments, the (initial) concentration of (sodium) chloride is 0.1 to 3.0 M.

In some embodiments, the range is 0.5 to 2.5 M.

In some embodiments, the range is 1.0 to 2.2 M.

In some embodiments, the (initial) concentration is about 2.0 M.

In some embodiments, there is a large molar excess of (sodium) chloride.

In some embodiments, the molar ratio of (sodium) chloride to salt, 7 or 8, is 5 to 100.

In some embodiments, the molar ratio is 20 to 80.

In some embodiments, the molar ratio is 50 to 80.

In some embodiments, the molar ratio is about 65.

In some embodiments, the recrystallisation includes subsequent drying of the recrystallised (highly crystalline) precipitate, for example, in an oven at a suitable temperature (e.g., 50 to 120° C.) for a suitable time (e.g., 1 to 24 hours).

For example, in some embodiments, crude MTC product or treated crude MTC product is dissolved in $H_2O$ at a concentration of about 0.03 M, and at approximately 65° C. Optionally, the solution is filtered. Sodium chloride is added. The mixture is allowed to cool, for example, to about room temperature, slowly, for example, over 1 to 10 hours. The resulting (highly crystalline) precipitate is collected, and optionally dried, for example, in an oven (e.g., at about 75° C.) for an appropriate time (e.g., about 16 hours).

Trituration (RX-TRIT):

In some embodiments, the recrystallisation is recrystallisation from water (e.g., from an aqueous solution or aqueous suspension) at an initial elevated temperature, in the presence of tetrahydrofuran (THF) (e.g., trituration).

In some embodiments, the (initial) concentration of salt 7 or 8 is 0.002 to 0.20 M.

In some embodiments, range is 0.01 to 0.20 M.

In some embodiments, range is 0.05 to 0.15 M.

In some embodiments, the (initial) concentration is about 0.13 M.

In some embodiments, the initial elevated temperature is 30 to 90° C.

In some embodiments, the range is 40 to 80° C.

In some embodiments, the range is 50 to 80° C.

In some embodiments, the initial elevated temperature is about 65° C.

In some embodiments, the ratio of water to THF is 20:1 to 2:1, by volume.

In some embodiments, the range is 10:1 to 2:1.

In some embodiments, the range is 7:1 to 3:1.

In some embodiments, the ratio is about 5:1.

In some embodiments, the recrystallisation includes subsequent drying of the recrystallised (highly crystalline) precipitate, for example, in an oven at a suitable temperature (e.g., 50 to 120° C.) for a suitable time (e.g., 1 to 24 hours).

For example, in some embodiments, crude MTC product or treated crude MTC product is dissolved in water at a concentration of about 0.13 M, and at approximately 65° C. Optionally, the solution is filtered. The mixture is allowed to cool slowly, and THF is added when the temperature reaches about 25° C., at a water:THF volume ratio of about 5:1. The mixture is again allowed to cool, for example, to about 5° C., slowly, for example, over 1 to 10 hours. The resulting (highly crystalline) precipitate is collected, and optionally dried, for example, in an oven (e.g., at about 100° C.) for an appropriate time (e.g., about 2 hours).

Compositions

One aspect of the present invention pertains to compositions comprising a diaminophenothiazinium compound, as described herein.

One aspect of the present invention pertains to compositions comprising a diaminophenothiazinium compound which is obtained by, or is obtainable by, a method as described herein.

In some embodiments, the composition further comprises a pharmaceutically acceptable carrier, diluent, or excipient.

Methods of Inactivating Pathogens

One aspect of the present invention pertains to use of a diaminophenothiazinium compound, as described herein, in a method of inactivating a pathogen in sample (for example a blood or plasma sample) the method comprising introducing the compound into the sample, and exposing the sample to light.

One aspect of the present invention pertains to use of a diaminophenothiazinium compound, which is obtained by, or is obtainable by, a method as described herein, in a method of inactivating a pathogen in sample (for example a blood or plasma sample) the method comprising introducing the compound into the sample, and exposing the sample to light.

Methods of Medical Treatment

One aspect of the present invention pertains to a diaminophenothiazinium compound, as described herein, for use in a method of treatment (e.g., of a disease condition) of the human or animal body by therapy.

One aspect of the present invention pertains to a diaminophenothiazinium compound, which is obtained by, or is obtainable by, a method as described herein, for use in a method of treatment (e.g., of a disease condition) of the human or animal body by therapy.

One aspect of the present invention pertains to use of a diaminophenothiazinium compound, as described herein, for the manufacture of a medicament for use in the treatment of a disease condition.

One aspect of the present invention pertains to use of a diaminophenothiazinium compound, which is obtained by, or is obtainable by, a method as described herein, for the manufacture of a medicament for use in the treatment of a disease condition.

One aspect of the present invention pertains to a method of treatment of a disease condition in a patient, comprising administering to said patient a therapeutically-effective amount of a diaminophenothiazinium compound, as described herein.

One aspect of the present invention pertains to a method of treatment of a disease condition in a patient, comprising administering to said patient a therapeutically-effective amount of a diaminophenothiazinium compound, which is obtained by, or is obtainable by, a method as described herein.

Disease Conditions

In some embodiments, the disease condition is a tauopathy.

A "tauopathy" is a condition in which tau protein (and aberrant function or processing thereof) plays a role. Alzheimer's Disease is an example of a tauopathy. The pathogenesis of neurodegenerative disorders such as Pick's disease and progressive supranuclear palsy (PSP) appears to correlate with an accumulation of pathological truncated tau aggregates in the dentate gyrus and stellate pyramidal cells of the neocortex, respectively. Other dementias include fronto-temporal dementia (FTD); fronto-temporal dementia with parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigroi luysian degeneration (PNLD); cortico-basal degeneration (CBD) and others (see, e.g., Wischik et al., 2000, especially Table 5.1 therein). Each of these diseases, which is characterized primarily or partially by abnormal tau aggregation, is referred to herein as a "tauopathy."

In some embodiments, the disease condition is Alzheimer's disease (AD).

In some embodiments, the disease condition is skin cancer.

In some embodiments, the disease condition is melanoma.

In some embodiments, the disease condition is viral, bacterial or protozoal.

In some embodiments, the protozoal disease condition is malaria. In this embodiment treatment may be in combination with another antimicrobial agent e.g. in combination with chloroquine or atovaquone.

In some embodiments, the viral disease condition is caused by Hepatitis C, HIV or West Nile virus.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Routes of Administration

The diaminophenothiazinium compound, or pharmaceutical composition comprising it, may be administered to a subject/patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal (including, e.g., intracatheter injection into the brain); by implant of a depot or reservoir, for example, subcutaneously or intramuscularly.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the diaminophenothiazinium compound to be used (e.g., administered) alone, it is often preferable to present it as a composition or formulation.

In some embodiments, the composition is a pharmaceutical composition (e.g., formulation, preparation, medicament) comprising a diaminophenothiazinium compound, as described herein, and a pharmaceutically acceptable carrier, diluent, or excipient.

In some embodiments, the composition is a pharmaceutical composition comprising at least one diaminophenothiazinium compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In some embodiments, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present invention pertains to methods of making a pharmaceutical composition comprising admixing at least one [$^{11}$C]-radiolabelled phenothiazine or phenothiazine-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 mg/ml, for example from about 10 ng/ml to about 1 mg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Examples of Preferred Formulations

One aspect of the present invention pertains to a dosage unit (e.g., a pharmaceutical tablet or capsule) comprising 20 to 300 mg of a diaminophenothiazinium compound as described herein (e.g., obtained by, or obtainable by, a method as described herein; having a purity as described herein; etc.), and a pharmaceutically acceptable carrier, diluent, or excipient.

In some embodiments, the dosage unit is a tablet.
In some embodiments, the dosage unit is a capsule.
In some embodiments, the amount is 30 to 200 mg.
In some embodiments, the amount is about 30 mg.
In some embodiments, the amount is about 60 mg.
In some embodiments, the amount is about 100 mg.
In some embodiments, the amount is about 150 mg.
In some embodiments, the amount is about 200 mg.

In some embodiments, the pharmaceutically acceptable carrier, diluent, or excipient is or comprises one or both of a glyceride (e.g., Gelucire 44/14 ®; lauroyl macrogol-32 glycerides PhEur, USP) and colloidal silicon dioxide (e.g., 2% Aerosil 200 ®; Colliodal Silicon Dioxide PhEur, USP).

Dosage

It will be appreciated by one of skill in the art that appropriate dosages of the diaminophenothiazinium compound, and compositions comprising the diaminophenothiazinium compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In some embodiments, the active compound (e.g., MTC) is administered to a human patient according to the following dosage regime: about 100 mg, 3 times daily.

In some embodiments, the active compound (e.g., MTC) is administered to a human patient according to the following dosage regime: about 150 mg, 2 times daily.

In some embodiments, the active compound (e.g., MTC) is administered to a human patient according to the following dosage regime: about 200 mg, 2 times daily.

EXAMPLES

The following are examples are provided solely to illustrate the present invention and are not intended to limit the scope of the invention, as described herein.

Example 1

Figure 2:
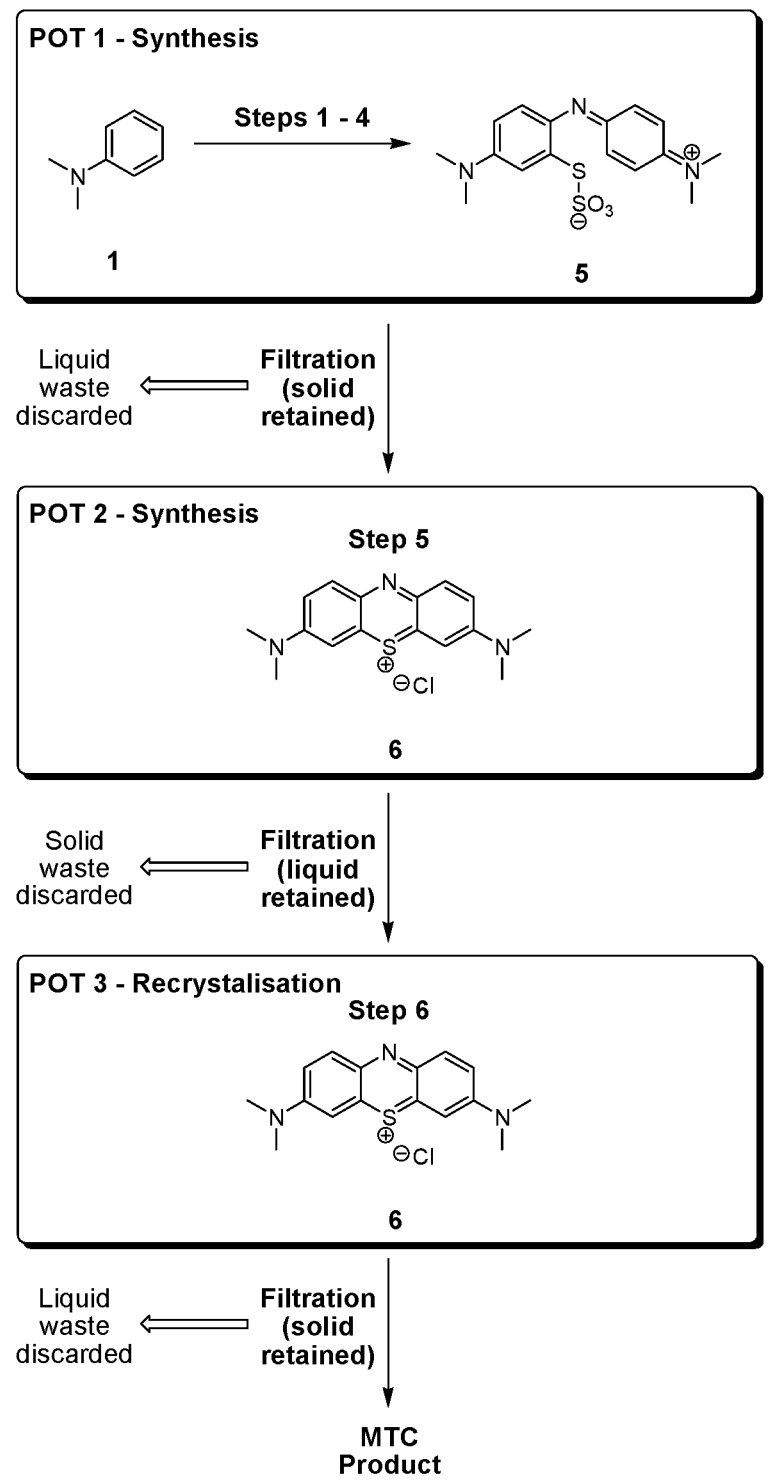
FIG. 2 shows a synthesis scheme for a 3-pot process.

This is a 3-pot method is depicted in FIG. 2.

Table 1 outlines the quantities of reagents and solvents used to produce MTC on a 10 g scale (i.e. starting from 10 g of dimethylaniline).

TABLE 1

| reagent quantities used at each synthetic step | | | | | |
|---|---|---|---|---|---|
| Substance | M.W. (g/mol) | Eq/Vol | mmols | Amount | Purity |
| Step 1 | | | | | |
| Dimethylaniline (1) | 121.18 | 1.0 eq | 82.52 | 10.00 g | ≥98.5% |
| Sodium nitrite | 69.00 | 1.1 eq | 91.30 | 6.30 g | ≥97.0% |
| Hydrochloric acid (32%) | — | 2.4 vol | — | 24.00 mL | Reagent |
| Water | — | 15.0 vol | — | 150.00 mL | Distilled |
| Step 2 | | | | | |
| Hydrochloric acid (32%) | — | 2.4 vol | — | 24.00 mL | Reagent |
| Iron (40-60 mesh) | 63.50 | 2.3 eq | 190.55 | 12.10 g | Reagent |
| Step 3 | | | | | |
| Aluminium sulphate hexadecahydrate | 630.39 | 0.15 eq | 12.38 | 7.80 | ≥95.0% |
| Sodium thiosulphate pentahydrate | 248.10 | 1.1 eq | 90.77 | 22.52 g | ≥99.5% |
| Sodium dichromate dihydrate | 298.00 | 0.41 eq | 33.83 | 10.08 g | ≥99.5% |
| Water | — | | | | Distilled |

TABLE 1-continued reagent quantities used at each synthetic step

Step 4

| | | | | | |
|---|---|---|---|---|---|
| Dimethylaniline | 121.18 | 1.0 eq | 82.52 | 10.00 g | ≥98.5% |
| Sulphuric acid | — | 0.44 vol | — | 4.40 mL | Reagent |
| Sodium dichromate dihydrate | 298.00 | 1.1 eq | 90.77 | 27.05 g | ≥99.5% |
| Scar-o-floc cellulose filter aid | — | — | — | 10.00 g | Reagent |
| Water | — | 18.0 vol | — | 180.00 mL | Distilled |

Step 5

| | | | | | |
|---|---|---|---|---|---|
| 0.01M Hydrochloric acid | — | 25.0 vol | — | 250.0 mL | Reagent |
| Copper sulphate pentahydrate | 249.69 | 0.1 eq | 8.25 | 2.06 g | 99% |

Step 6

| Substance | M.W (g/mol) | Eq/Vol | moles | Amount | Purity |
|---|---|---|---|---|---|
| Sodium chloride | 58.44 | 20.72 eq | 1.71 | 100.00 g | >99.5 |
| Water | — | 40.0 vol | — | 400.00 mL | Distilled |
| | Overall yield | | | 55% (46%) [method 1] | |
| | | | | 44% (39%) [method 2] | |

Yields in brackets account for the starting material and/or product purity

Synthesis of N,N-dimethyl-p-phenylene diamine (Compound 3, Steps One and Two)

To a 3 necked 1 liter round bottom flask fitted with a dropping funnel and thermometer, and held in an ice bath, water (100 mL) and dimethylaniline (MW 121.18, 10.00 g, 82.52 mmol) were added. The mixture was stirred until the temperature was 5° C. (±2° C.), and concentrated hydrochloric acid (32%, 24.00 mL, 2.4 vol.) added over a period of 5 minutes. Once the temperature had returned to 5° C. (±2° C.), and the dimethylaniline was fully dissolved, a solution of sodium nitrite (MW 69.00, 6.30 g, 91.30 mmol) in water (50 mL, 5.0 vol.) was added to the dropping funnel. The colourless solution was added drop-wise over a period of 25 minutes, which led to the reaction mixture turning cloudy and orange. Upon completion of the addition the mixture was stirred for 1 hour at 5° C. (±2° C.). At the end of this period step 2 commenced. Concentrated hydrochloric acid (32%, 24.0 mL, 2.4 vol.) was added to the mixture in one portion. Portion-wise addition of iron (MW 63.50, 12.10 g, 190.55 mmol) then commenced over a period of 25 minutes. During addition, bubbling foam was observed on the surface of the mixture and the temperature rose to 10° C. On completion of iron addition the mixture was left to stir, held at a temperature of 10-12° C. for 2 hours. Typically, the reaction was left stirring overnight, and a dark red-brown solution was obtained.

Synthesis of the Thiosulphonic Acid of N,N-dimethyl-p-phenylene diamine (Compound 4, Step Three)

Reaction continued in the same vessel as described above, without filtration of the iron residues. The round bottom flask was held in an ice bath to lower the temperature to 5° C. (±2° C.). Aluminium sulphate hexadecahydrate (MW 630.39, 7.80 g, 12.38 mmol) was added as a dry solid, and the mixture left to stir for 5 minutes to allow dissolution to occur. A solution of sodium thiosulphate pentahydrate (MW 248.10, 22.52 g, 90.77 mmol) in water (25.0 mL, 2.5 vol.) was then added, in one portion, and the mixture stirred for a further 5 minutes. A solution of sodium dichromate dihydrate (MW 298.00, 10.08 g, 33.83 mmol) in water (40.0 mL, 4.0 vol.) was then added to the dropping funnel, and the solution added to the reaction mixture drop-wise over a 25 minute period. During this process the temperature of the mixture increased slightly (usually to 9° C.). On completion of the addition process, the reaction mixture was stirred for 1 hour. At the end of this period, the next step was performed directly in the same flask.

Synthesis of the Thiosulphonic Acid of Bindschedler's Green (Compound 5, Step Four)

A solution of dimethylaniline (MW 121.18, 10.00 g, 82.52 mmol), water (10.0 mL, 1.0 vol.) and sulphuric acid was prepared by the portion-wise addition of sulphuric acid to an ice-cooled mixture of dimethylaniline and water. The temperature was monitored throughout addition such that it was not allowed to rise above 15° C. On addition of the final portion of acid, the solution was left to chill to 5° C. (±2° C.). The solution was then added to the reaction mixture in one portion, and a solution of sodium dichromate dihydrate (MW 298.00, 27.05 g, 90.77 mmol) in water (70.0 mL, 7.0 vol.) added to the dropping funnel. Drop-wise addition of the dichromate solution was performed over a 25 minute period, and the addition process was accompanied by a purple surface sheen and green colouration appearing in the bulk reaction mixture. The mixture was then left stirring at 5° C. (±2° C.) for 2 hours. At the end of this period, SCAR-O-FLOC cellulose filter agent (10.0 g) was added to the flask, and the mixture stirred until a smooth slurry had formed. The slurry was then filtered, and the residue washed with water (100.0 mL, 10.0 vol.). The residue was used directly in the next step without further treatment.

Synthesis of the Methylthioninium Chloride (Compound 6, Step Five)

The green residue obtained was re-slurried in 0.01 M hydrochloric acid (250.0 mL, 25.0 vol.) and returned to a 1 liter round bottom flask fitted with a thermometer, condenser and stopper. Copper sulphate pentahydrate (MW 249.69, 2.06 g, 8.25 mmol) was added to the slurry in the flask, and the dark green mixture heated to 85° C. for 1 hour. At the end of this period the mixture had turned dark blue, indicating that methylene blue had formed.

Isolation of Methylthioninium Chloride (Compound 6, Step Six) by "Salting Out"

The reaction mixture was filtered hot (at reaction temperature, 85° C.) yielding a dark blue filtrate and dark blue residue. The residue was then washed with hot water (~60 C, 4×100.0 mL, 4×10.0 vol.) and the combined filtrates added to a beaker.

Sodium chloride (MW 58.44, 100.00 g, 1.71 mol) was added to the combined filtrates in a beaker and the mixture was placed on a warm, but turned off, hotplate and left to stir for a minimum of three hours, but typically overnight, to allow MTC to crystallise out.

The product was then isolated by filtration yielding a dark green/blue/gold solid, which was dried in a vacuum oven at 50° C. for 16 hours.

MTC was obtained in 55% yield (52%). [The yield in brackets accounts for reagent and/or product purity.]

Example 2

The process of Example 1 was scaled up to use 20 g of dimethylaniline. At the end of synthesis (using a sodium chloride "salting out" process) MTC was obtained in 63% yield (56%). [The yield in brackets accounts for reagent and/or product purity.]

Example 3

The process of Example 1 was used, except that the isolation of MTC (final step) was achieved by the following process.

The reaction mixture was filtered hot (at reaction temperature, 85° C.) yielding a dark blue filtrate and dark blue residue. The residue was then washed with hot water (~60° C., 4×100.0 mL, 4×10.0 vol.) and the combined filtrates added to a beaker.

The pH of the combined filtrates would be adjusted to pH=1 using concentrated hydrochloric acid, and the mixture left stirring at ambient temperature for a minimum of three hours, but typically overnight, to allow MTC to crystallise out.

The product was then isolated by filtration yielding a dark green/blue/gold solid, which was dried in a vacuum oven at 50° C. for 16 hours.

MTC was obtained in 44% yield (39%).

Example 4

The process of Example 3 was scaled up to use 20 g of dimethylaniline, with the exception that a 25.0 vol. slurry volume was utilised at step five. At the end of synthesis (using a hydrochloric acid "salting out" process) MTC was obtained in 56% yield (50%)

Example 5a

Figure 3:
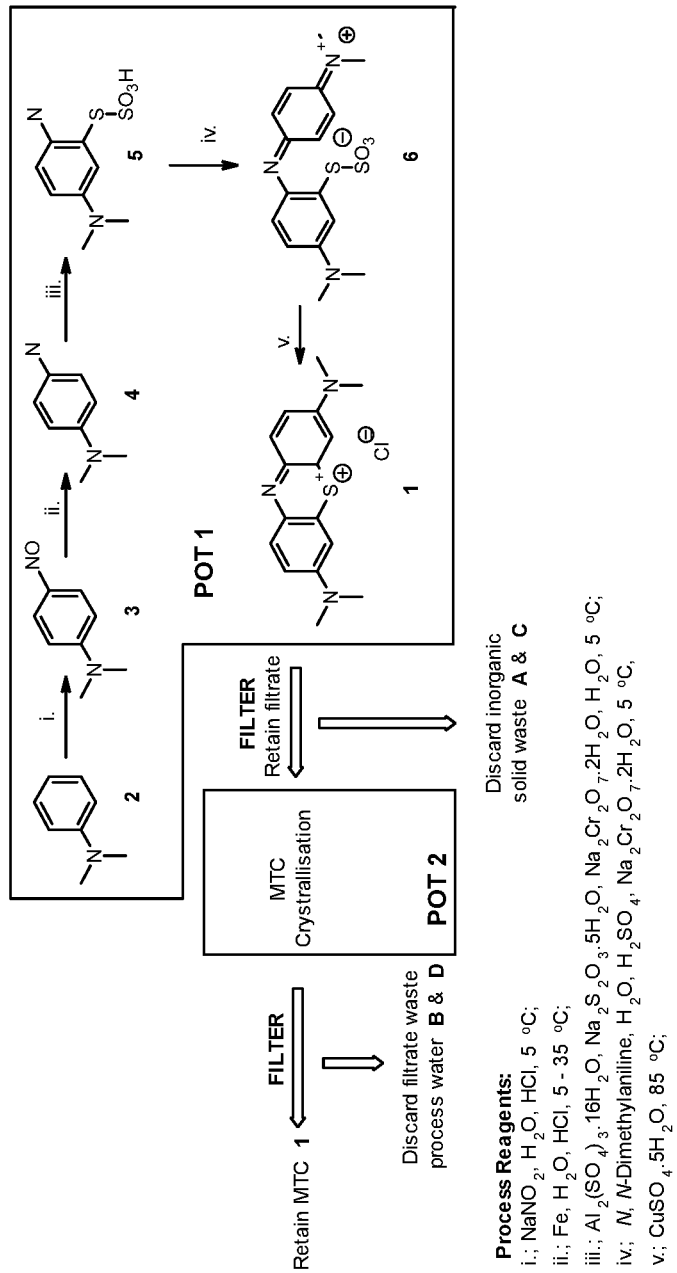
FIG. 3 shows a synthesis scheme for a 2-pot process.

This is a 2-pot method is shown in FIG. 3

Table 2a outlines the quantities of reagents and solvents used to produce MTC on a 10 g scale (i.e. starting from 10 g of dimethylaniline) using the method of Example 5a.

TABLE 2a

Reagent quantities

| Substance | M.W. (g/mol) | Eq/Vol | moles | Amount | Purity |
|---|---|---|---|---|---|
| Step 1 | | | | | |
| N,N-Dimethylaniline (2) | 121.19 | 1.0 eq. | 0.0825 | 10.0 g | 99% |
| Water | — | 15 vol. | — | 150 ml | De-ionised |
| Hydrochloric Acid | — | 2.4 vol. | — | 24 ml | 32% |
| Sodium Nitrite | 69.0 | 1.1 eq. | 0.0913 | 6.3 g | 98% |
| Water | — | 5.0 vol. | — | 50 ml | De-ionised |
| Nitroso (3) | 150.08 | 1.0 eq. | 0.0825 | 12.38 g | Not isolated |
| | | | | Yield >95% | Not isolated |
| Step 2 | | | | | |
| Hydrochloric acid | — | 2.4 vol. | — | 24 ml | 32% |
| Iron Filings | 55.85 | 2.63 eq. | 0.217 | 12.1 g | Reagent |
| Amine (4) | 136.10 | 1.0 eq. | 0.0825 | 11.23 g | Not isolated |
| | | | | Yield >95% | Not isolated |
| Step 3 | | | | | |
| Aluminium Sulphate | 342.14 (Anhyd) 630.42(16H$_2$O) | 0.5 eq. | 0.412 | 26.0 g | 96% 16H$_2$O |
| Sodium Thiosulphate | 248.18 | 1.10 eq. | 0.0907 | 22.5 g | ≥99.5% 5H$_2$O |
| Water | — | 2.5 vol. | — | 25 ml | De-ionised |
| Sodium Dichromate | 298.00 (2H$_2$O) | 0.41 eq. | 0.0336 | 10.0 g | ≥99.5% 2H$_2$O |
| Water | — | 4.0 vol. | — | 40 ml | De-ionised |
| Thiosulphonic Acid (5) | 248.32 | 1.0 eq. Yield - | 0.0825 Not isolated | 20.49 g | Not isolated |
| Step 4 | | | | | |
| N,N-Dimethylaniline | 121.19 | 1.0 eq. | 0.0825 | 10.0 g | 99% |
| Water | — | 1.0 vol. | — | 10 ml | De-ionised |
| Sulphuric acid | — | 0.8% w/w | — | 8.0 g | >98% |
| Sodium Dichromate | 298.00 (2H2O) | 1.06 eq. | 0.0872 | 26.0 g | ≥99.5% 2H$_2$O |
| Water | — | 7.0 vol. | — | 70 ml | De-ionised |
| Thiosulphonic acid of BG (6) | 365.09 | 1.0 eq. | 0.0825 | 30.12 g | Not isolated |
| | | Yield - | | | Not isolated |

TABLE 2a-continued

Reagent quantities

| Substance | M.W. (g/mol) | Eq/Vol | moles | Amount | Purity |
|---|---|---|---|---|---|
| Step 5 | | | | | |
| Copper (II) Sulphate | 249.70 | 0.097 | 0.0080 | 2.0 | 99% |
| Water | — | 13 vol. | — | 130 ml | De-ionised |
| Hydrochloric acid | — | 0.65 vol. | — | ~6.5 ml | 32% |
| MTC (1) | 319.85 (Anhyd) | 1.0 | 0.0825 | 26.39 | (≥95%) |
| Overall yield | | | | 40% | |

To a round bottom flask (RBF) was added N,N-dimethylaniline ($C_6H_5N(CH_3)_2$, MW 121.2, 10 g, 0.0825 mol), water (150 cm$^3$), and HCl (32%, 24 cm$^3$). The mixture was cooled to ~5° C. To this mixture was added dropwise an aqueous solution of sodium nitrite (NaNO$_2$, MW 69.0, 6.3 g, 00.0913 mol) in water (100 cm$^3$) over a 25 minute period. The resulting suspension was stirred at a low temperature (5-10° C.) for 1 hour. The mixture was cooled to approximately ~5° C. HCl (32%, 24 cm$^3$) were added in one aliquot. Iron fillings (Fe, MW 55.85, 12.1 g, 0.217 mol) were added in one aliquot portions. The mixture was stirred for 2 hours at a temperature below 30° C.

The mixture was cooled to approximately 5° C. The mixture was treated with aluminium sulphate hexadecahydrate ($Al_2(SO_4)_3 \cdot 16H_2O$, MW 630.42, 26 g, 0.412 mol). The mixture was treated with a solution of sodium thiosulfate pentahydrate ($Na_2S_2O_3 \cdot 5H_2O$, MW 248.2, 22.5 g, 0.0907 mol) in water (25 cm$^3$). A solution of sodium dichromate dihydrate ($Na_2Cr_2O_7 \cdot 2H_2O$, MW 298.0, 10.0 g, 0.0336 mmol) in water (40 cm$^3$) was added dropwise over a 30 minute period. The solution was then stirred at low temperature (about 5° C.) for 1 hour. A homogenous solution of N,N-dimethylaniline ($C_6H_5N(CH_3)_2$, MW 121.2, 10 g, 0.0825 mol), water (10 cm$^3$) and $H_2SO_4$ (98%, 8 g) was then added to the chilled solution. Then, a solution of sodium dichromate dihydrate ($Na_2Cr_2O_7 \cdot 2H_2O$, MW 298.0, 26.0 g, 0.0872 mmol) in water (70 cm$^3$) was added dropwise over a 30 minute period. The mixture was stirred at approximately 5° C. for 2 hours.

Copper (II) sulfate pentahydrate ($CuSO_4 \cdot 5H_2O$, MW 249.7, 2.06 g, 8.25 mmol) is added to the reaction mixture. The temperature was increased to 85° C. The mixture was stirred at this temperature for 1 hour. A deep blue colour was formed. The mixture was cooled to room temperature. The mixture was filtered. The residue was washed with water (2×80 cm$^3$). The filtrate was collected. The filtrate was treated with hydrochloric acid to obtain a pH of 1, this precipitates out the crude methylthioninium chloride. The mixture was stirred until the deep blue colour disappeared. The mixture was filtered to provide crude methylthioninium chloride (MTC) as a solid (10.62 g, 40%—based on anhydrous weight).

Example 5b

Figure 4:
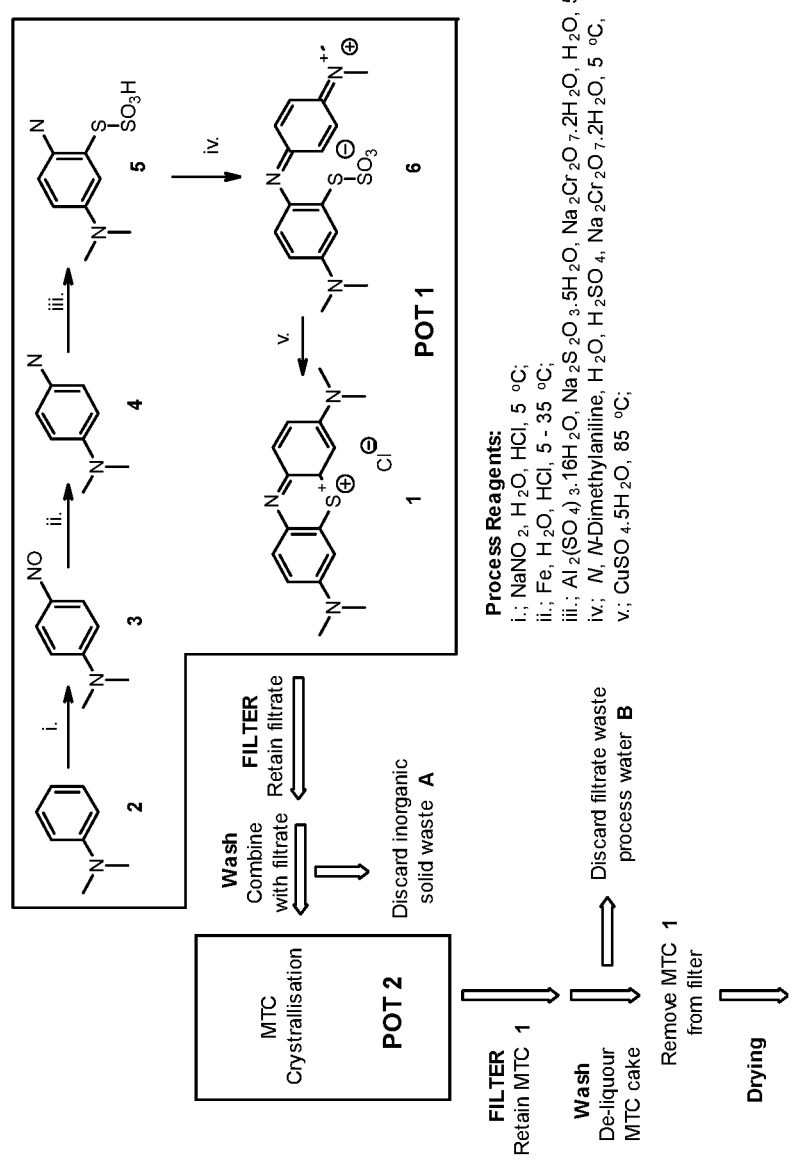
FIG. 4 shows a synthesis scheme for a 2-pot process.

This is a 2-pot method is depicted in FIG. 4.

Table 2b outlines the quantities of reagents and solvents used to produce MTC on a 10 g scale (i.e. starting from 10 g of dimethylaniline) using the method of Example 5b.

TABLE 2b

Reagent quantities

| Substance | M.W. (g/mol) | Eq/Vol | moles | Amount | Purity |
|---|---|---|---|---|---|
| Step 1 | | | | | |
| N,N-Dimethylaniline (2) | 121.19 | 1.0 eq. | 0.0825 | 10.0 g | 99% |
| Water | — | 15 vol. | — | 150 ml | De-ionised |
| Hydrochloric Acid | — | 2.4 vol. | — | 24 ml | 32% |
| Sodium Nitrite | 69.0 | 1.1 eq. | 0.0913 | 6.3 g | 98% |
| Water | — | 5.0 vol. | — | 50 ml | De-ionised |
| Nitroso (3) | 150.08 | 1.0 eq. | 0.0825 | 12.38 g Yield >95% | Not isolated Not isolated |
| Step 2 | | | | | |
| Hydrochloric acid | — | 2.4 vol. | — | 24 ml | 32% |
| Iron Filings | 55.85 | 2.63 eq. | 0.217 | 12.1 g | Reagent |
| Amine (4) | 136.10 | 1.0 eq. | 0.0825 | 11.23 g Yield >95% | Not isolated Not isolated |
| Step 3 | | | | | |
| Aluminium Sulphate | 342.14 (Anhyd) 630.42(16H$_2$O) | 0.5 eq. | 0.412 | 26.0 g | 96% 16H$_2$O |
| Sodium Thiosulphate | 248.18 | 1.10 eq. | 0.0907 | 22.5 g | ≥99.5% 5H$_2$O |
| Water | — | 2.5 vol. | — | 25 ml | De-ionised |
| Sodium Dichromate | 298.00 (2H$_2$O) | 0.41 eq. | 0.0336 | 10.0 g | ≥99.5% 2H$_2$O |

TABLE 2b-continued

| | Reagent quantities | | | | |
|---|---|---|---|---|---|
| Substance | M.W. (g/mol) | Eq/Vol | moles | Amount | Purity |
| Water | — | 4.0 vol. | — | 40 ml | De-ionised |
| Thiosulphonic Acid (5) | 248.32 | 1.0 eq. | 0.0825 | 20.49 g | Not isolated |
| | | | | Yield - | Not isolated |
| Step 4 | | | | | |
| N,N-Dimethylaniline | 121.19 | 1.0 eq. | 0.0825 | 10.0 g | 99% |
| Water | — | 1.0 vol. | — | 10 ml | De-ionised |
| Sulphuric acid | — | 0.8% w/w | — | 8.0 g | >98% |
| Sodium Dichromate | 298.00 (2H$_2$O) | 1.06 eq. | 0.0872 | 26.0 g | ≥99.5% 2H$_2$O |
| Water | — | 7.0 vol. | — | 70 ml | De-ionised |
| Thiosulphonic acid of BG (6) | 365.09 | 1.0 eq. | 0.0825 | 30.12 g | Not isolated |
| | | | | Yield - | Not isolated |
| Step 5 | | | | | |
| Copper (II) Sulphate | 249.70 | 0.097 | 0.0080 | 2.0 | 99% |
| Water | — | 40 vol. | — | 400 ml | De-ionised |
| Hydrochloric acid | — | 0.65 vol. | — | ~6.5 ml | 32% |
| MTC (1) | 319.85 (Anhyd) | 1.0 | 0.0825 | 26.39 (≥95%) | — |
| Overall yield | | | | 48% | |

Step i
1. N,N-dimethylaniline (10.0 g, 0.0825 mol) is added to the reaction flask.
2. A mixture of 32% hydrochloric acid (24 cm$^3$) and water (150 cm$^3$) is added to the reaction flask.
3. The solution is stirred to ensure homogeneity.
4. The reaction mixture is cooled to 5° C. (±2° C.).
5. A solution of an aqueous sodium nitrite [(6.3 g, 0.0913 mol) in water (50 cm$^3$)] is added over 30 mins. A maximum temperature of 10° C. will be observed, during which a brown reaction mixture with orange precipitate is obtained.
6. The reaction is to be stirred for an additional 60 minutes, whilst maintaining a temperature of 5 OC (±2° C.).

Step ii
7. Addition of 32% hydrochloric acid (24 cm$^3$)
8. Addition of iron filings (12.1 g, 0.217 mol) over 60 minutes ensuring temperature remains below 35° C.
9. The reaction is left to stir for approximately 17 hrs. (±1 hr.), at approx. 20° C. During this time the orange precipitate disappears, foam of the reaction mixture will occur and an homogenous brown reaction liquor containing residual iron filings remains.).
[TLC Method: neutralise a sample of reaction mixture with NaHCO$_3$ and extract into ethyl acetate, spot the ethyl acetate layer and run the TLC with ethyl acetate, hexane 1:3. The nitroso runs with an Rf=~0.3 (orange spot) and the diamine on the baseline (brown spot)].

Step iii
10. The reaction mixture is cooled to 5° C. (±1 C. °)
11. Addition of solid aluminium sulphate (26.0 g, 0.0423 mol).
12. The reaction mixture is stirred for 5 minutes
13. Addition of sodium thiosulphate solution [(22.5 g, 0.0907 mol) in water (25 cm$^3$)] in one aliquot.
14. The reaction mixture is stirred for five minutes
15. Addition of sodium dichromate solution [(10.0 g, 0.0336 mol) in water (40 cm$^3$) drop wise over 30 minutes. A temperature of no high than 12° C. (±1 C. °) is maintained. Brown precipitate appears during this step, with a slight lightening in the colour of the brown reaction mixture.
16. The reaction is stirred for 1 hr. at 5° C. (±2° C.).

Step iv
17. A solution of N,N-dimethylaniline [(10.0 g, 0.0825 mol) in water (10 cm$^3$) and sulphuric acid (8 g)] is prepared by adding sulphuric acid drop wise to a chilled N,N-dimethylaniline and water mixture. Caution must be taken during the acid addition as this is extremely exothermic.
18. The N,N-dimethylaniline [(10.0 g, 0.0825 mol) in water (10 cm$^3$) and sulphuric acid (8 g)] solution is then added to the reaction flask as one aliquot.
19. Addition of a solution of sodium dichromate [(26.0 g, 0.0872 mol) in water (70 cm$^3$)] drop wise over 30 mins, whilst maintaining the temperature below 12° C.
20. The reaction is stirred for an additional 2 hrs. 5° C. (±2° C.).
21. Addition of 10 g of cellulose filter aid (BW SCAR-O-FLOC).

Step v
22. Addition of copper sulphate (2.0 g, 8.03 mmol).
23. The reaction is heated to 85° C. and stirred for 1 hr. The reaction will turn metallic purple, then blue.
24. The insolubles are collected by filtration whilst still at 85° C.
25. The filter cake is washed with pre-heated (60° C.) water (4×100 cm$^3$). Each filtrate from a wash is combined with the reaction filtrate. [A resting time, of at least 2 minutes, between the addition of the wash into the filter, and pulling the wash through the filter cake, allows the cake to thoroughly soak.]
26. The combined filtrate is cooled to 20° C.
27. The filtrate is adjusted to pH 1 using (32%) hydrochloric acid (approx. 12 cm$^3$).
28. The filtrate is stirred for an additional 18 hours to ensure complete crystallisation.
29. The crystalline methylthioninium chloride is collected by vacuum filtration.
30. The filter cake is washed with pre-chilled (5° C.); acidified (pH 1) water (2×20 cm$^3$).
31. The crystalline methylthioninium chloride is dried in an oven at 40° C. for 18 hours.
Yield=48% (±3%) *

*(Yield taking into account salts, organic impurities, and water content)

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as described herein.

The present invention is not limited to those embodiments that are encompassed by the appended claims, which claims pertain to only some of many preferred aspects and embodiments of the invention.

What is claimed is:

1. A method of synthesis comprising one or more of the steps of, in order:

nitrosylation (NOS), in which an N,N-disubstituted-3-optionally substituted aniline, 1, is 4-nitrosylated to give said N,N-disubstituted-3-optionally substituted-4-nitrosyl aniline, 2:

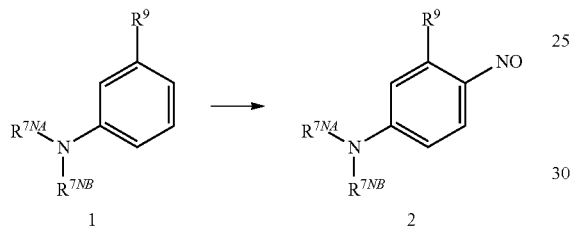

nitrosyl reduction (NR), in which an N,N-disubstituted-3-optionally substituted-4-nitrosyl aniline, 2, is reduced to form said N,N-disubstituted-1,4-diamino-5-optionally substituted benzene, 3:

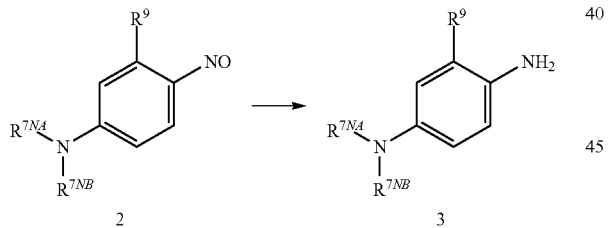

thiosulfonic acid formation (TSAF), in which an N,N-disubstituted-1,4-diamino-5-optionally substituted benzene, 3, is oxidized in the presence of a thiosulfate to give said thiosulfuric acid S-{2-(amino)-3-(optionally substituted)-5-(disubstituted-amino)-phenyl} ester, 4:

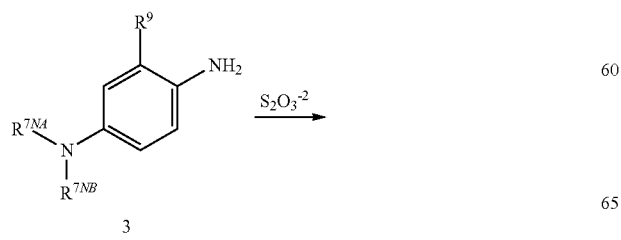

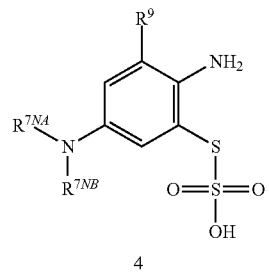

oxidative coupling (OC), in which a thiosulfuric acid S-{2-(amino)-3-(optionally substituted)-5-(disubstituted amino)-phenyl} ester, 4, is oxidatively coupled to an N,N-disubstituted-3-optionally substituted-aniline, 5, using an oxidizing agent that is or comprises Cr(VI), to give a [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6:

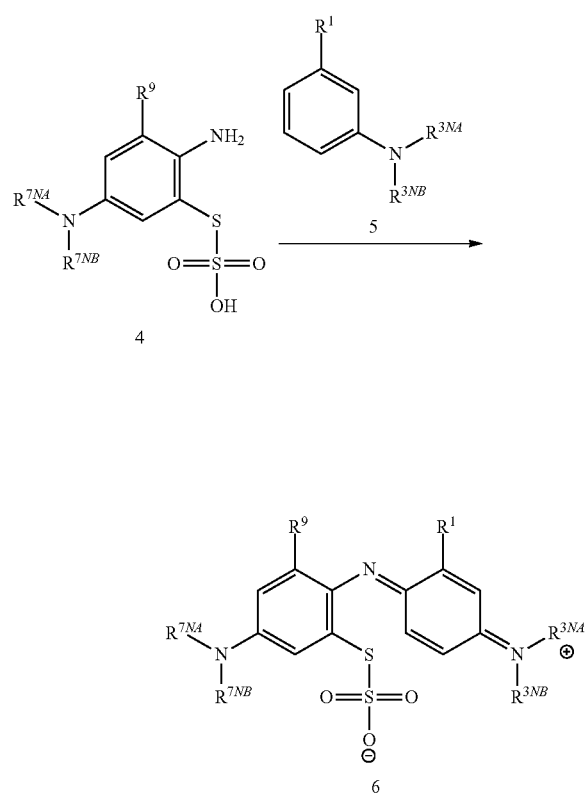

Cr(VI) Reduction (CR), in which the product of the oxidative coupling (OC) step is treated to convert residual Cr(VI) to Cr(III), ring closure (RC), in which said isolated and purified [4-{2-(thiosulfate)-4-(disubstituted amino)-6-(optionally substituted)-phenyl-imino}-3-(optionally substituted)-cyclohexa-2,5-dienylidene]-N,N-disubstituted ammonium, 6, is subjected to ring closure to give a 3,7-bis(disubstituted-amino)-1,9-(optionally substituted)-phenothiazin-5-ium salt, 7:

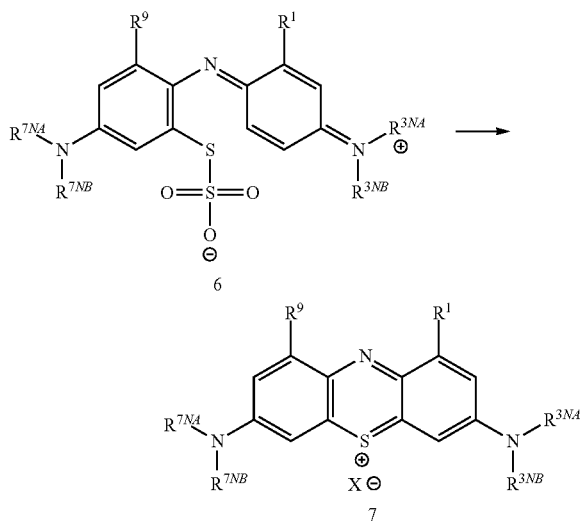

6

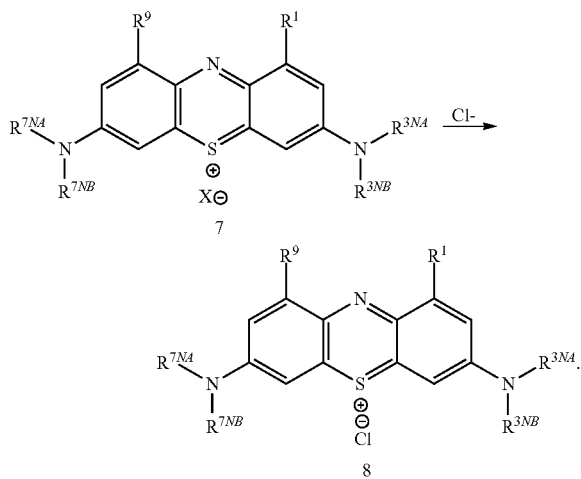

7 chloride salt formation (CSF), in which said 3,7-bis(disubstituted-amino)-1,9-(optionally substituted)-phenothiazin-5-ium salt, 7, is reacted with chloride, to give a 3,7-bis(disubstituted-amino)-1,9-(optionally substituted)-phenothiazin-5-ium chloride salt, 8:

7

8 wherein the method comprises at least one filtration, and wherein a filtration agent is added to the reaction pot prior to that filtration.

2. A method according to claim 1, wherein the filtration agent is or comprises cellulose.

3. A method according to claim 1, wherein at least the nitrosyl reduction (NR) step, the thiosulfonic acid formation (TSAF) step and the oxidative coupling (OC) step are performed and are all completed in the same pot.

4. A method according to claim 3, wherein the filtration agent is added to the reaction vessel in which the nitrosyl reduction (NR), thiosulfonic acid formation (TSAF), and oxidative coupling (OC) steps are completed.

5. A method according to claim 1, wherein at least the thiosulfonic acid formation (TSAF) step is performed further comprising addition of an activating agent prior to or during the thiosulfonic acid formation (TSAF) step, wherein the activating agent preferably comprises aluminium sulphate.

6. A method according to claim 5, wherein the activating agent is or comprises aluminium sulphate hexadecahydrate.

7. A method of synthesis according to claim 1, wherein at least the thiosulfonic acid formation (TSAF) step is performed and the oxidation in said thiosulfonic acid formation (TSAF) step is by reaction with an oxidizing agent that is or comprises Cr(VI).

8. A method of synthesis according to claim 1, wherein at least the thiosulfonic acid formation (TSAF) step is performed and the thiosulfate is or comprises $Na_2S_2O_3$.

9. A method of synthesis according to claim 1, wherein at least the nitrosyl reduction (NR) is performed and the reduction in said nitrosyl reduction (NR) step is by reaction with a reducing agent that is or comprises Fe(0).

10. A method according to claim 9, wherein said reduction in said nitrosyl reduction (NR) step is by reaction with a reducing agent that is or comprises metallic iron.

11. A method according to claim 10, wherein metallic iron is used in excess, and wherein the excess metallic iron is not removed from the reaction mixture after reaction completion.

12. A method according to claim 3 wherein the nitrosylation step (NOS) is completed in the same reaction vessel as the nitrosyl reduction (NR), thiosulfonic acid formation (TSAF), and oxidative coupling (OC) steps.

13. A method according to claim 3, wherein the ring closure (RC) step is completed in the same reaction vessel as the nitrosyl reduction (NR), thiosulfonic acid formation (TSAF), and oxidative coupling (OC) steps.

14. A method according to claim 2, wherein at least the nitrosyl reduction (NR) step, the thiosulfonic acid formation (TSAF) step and the oxidative coupling (OC) step are performed and are all completed in the same pot.

15. A method according to claim 14, wherein the filtration agent is added to the reaction vessel in which the nitrosyl reduction (NR), thiosulfonic acid formation (TSAF), and oxidative coupling (OC) steps are completed.

16. A method according to claim 2, wherein at least the thiosulfonic acid formation (TSAF) step is performed further comprising addition of an activating agent prior to or during the thiosulfonic acid formation (TSAF) step, wherein the activating agent preferably comprises aluminium sulphate.

17. A method according to claim 16, wherein the activating agent is or comprises aluminium sulphate hexadecahydrate.

18. A method of synthesis according to claim 2, wherein at least the thiosulfonic acid formation (TSAF) step is performed and the oxidation in said thiosulfonic acid formation (TSAF) step is by reaction with an oxidizing agent that is or comprises Cr(VI).

19. A method of synthesis according to claim 2, wherein at least the thiosulfonic acid formation (TSAF) step is performed and the thiosulfate is or comprises $Na_2S_2O_3$.

20. A method of synthesis according to claim 2, wherein at least the nitrosyl reduction (NR) is performed and the reduction in said nitrosyl reduction (NR) step is by reaction with a reducing agent that is or comprises Fe(0).

21. A method according to claim 20, wherein said reduction in said nitrosyl reduction (NR) step is by reaction with a reducing agent that is or comprises metallic iron.

22. A method according to claim 21, wherein metallic iron is used in excess, and wherein the excess metallic iron is not removed from the reaction mixture after reaction completion.

23. A method according to claim 14 wherein the nitrosylation step (NOS) is completed in the same reaction vessel as the nitrosyl reduction (NR), thiosulfonic acid formation (TSAF), and oxidative coupling (OC) steps.

24. A method according to claim 14, wherein the ring closure (RC) step is completed in the same reaction vessel as the nitrosyl reduction (NR), thiosulfonic acid formation (TSAF), and oxidative coupling (OC) steps.

25. A method according to claim 12, wherein the ring closure (RC) step is completed in the same reaction vessel as the nitrosyl reduction (NR), thiosulfonic acid formation (TSAF), and oxidative coupling (OC) steps.

26. A method according to claim 23, wherein the ring closure (RC) step is completed in the same reaction vessel as the nitrosyl reduction (NR), thiosulfonic acid formation (TSAF), and oxidative coupling (OC) steps.

* * * * *